United States Patent [19]

Holmes, II et al.

[11] Patent Number: 5,371,687
[45] Date of Patent: Dec. 6, 1994

[54] GLUCOSE TEST DATA ACQUISITION AND MANAGEMENT SYSTEM

[75] Inventors: John S. Holmes, II, Indianapolis; Joe E. Anderson, Greenwood, both of Ind.

[73] Assignee: Boehringer Mannheim Corporation, Indianapolis, Ind.

[21] Appl. No.: 979,634

[22] Filed: Nov. 20, 1992

[51] Int. Cl.$^5$ ............................................. H05K 7/16
[52] U.S. Cl. ................................. 364/514; 364/413.02; 340/825.06; 361/622; 361/682; 361/686
[58] Field of Search .............. 364/146, 413.01, 413.02, 364/413.03, 413.07, 514, 550, 492, 506; 361/331, 332, 334, 342, 344, 380, 390-394; 340/825.06, 825.19

[56] References Cited

U.S. PATENT DOCUMENTS

| | | |
|---|---|---|
| 3,872,448 | 3/1975 | Mitchell, Jr. |
| 3,881,992 | 5/1975 | Ralston |
| 3,907,503 | 9/1975 | Betts et al. |
| 3,980,437 | 9/1976 | Kishimoto et al. |
| 3,989,383 | 11/1976 | Paulson |
| 4,093,849 | 6/1978 | Baxter, Jr. et al. |
| 4,118,687 | 10/1978 | McWaters et al. |
| 4,121,574 | 10/1978 | Lester |
| 4,160,646 | 7/1979 | Furutani et al. |
| 4,168,469 | 9/1979 | Parikh et al. |
| 4,309,112 | 1/1982 | Ashley et al. |
| 4,509,859 | 4/1985 | Markart et al. |
| 4,519,398 | 5/1985 | Lisiecki et al. |
| 4,523,297 | 6/1985 | Ugon et al. |
| 4,546,436 | 10/1985 | Schneider et al. |
| 4,571,702 | 2/1986 | DeArras |

(List continued on next page.)

FOREIGN PATENT DOCUMENTS

| | | |
|---|---|---|
| 387630A2 | 9/1990 | European Pat. Off. |
| 2319465 | 10/1973 | Germany |
| 63-61147 | 3/1988 | Japan |
| 63-269046 | 11/1988 | Japan |

OTHER PUBLICATIONS

Diabetes, vol. 33, Supplement 1, issued May 24, 1984, D. Michaels, et al., "A Memory-Glucose Reflectance Meter for Automatic Data Recording," entry 498, p. 103A.

Diabetes, vol. 33, Supplement 1, issued May 1984, J. Silverstein et al., "Comparison of Systems for Blood Glucose Monitoring with a Meter: Accu-Chek and Glucometer," entry 502 p. 131A.

Diabetes, vol. 33, Supplement 1, issued May 1984, D. Hiennen et al., "Assessment of Accuracy of 11 Glucose Machines for Home Use," entry 503 p. 131A.

Diabetes, vol. 33, Supplement 1, issued May 1984, V. G. Kuykendall et al., "Information Management for Glucometer Reflectance Photometer with Memory," entry 507, p. 132A.

Primary Examiner—Jack B. Harvey
Assistant Examiner—Edward Pipala
Attorney, Agent, or Firm—Barnes & Thornburg

[57] ABSTRACT

A system is provided for adapting one of a number of different types of instruments to a common protocol. Each instrument has a serial input-output (I/O) port, a control for the serial I/O port, and an input for operating power to the instrument. The system includes a different type of housing for each different type of instrument. Each different type of housing includes openings through which selected controls and displays of a respective one of the instruments are accessible. Each different type of housing includes couplers for coupling to a respective type of instrument's serial I/O port, and to a respective type of instrument's operating power input, and a data processing module including a first multiple conductor. Each type of housing includes a complementary second multiple conductor connector for connecting to the first multiple conductor connector when a respective housing is mated to the data processing module.

29 Claims, 20 Drawing Sheets

U.S. PATENT DOCUMENTS

| | | |
|---|---|---|
| 4,676,653 | 6/1987 | Strohmeier et al. . |
| 4,685,059 | 8/1987 | Yamamoto . |
| 4,715,385 | 12/1987 | Cudahy et al. . |
| 4,731,726 | 3/1988 | Allen, III . |
| 4,747,060 | 5/1988 | Sears, III et al. . |
| 4,751,648 | 6/1988 | Sears, III et al. . |
| 4,779,199 | 10/1988 | Yoneda et al. . |
| 4,791,461 | 12/1988 | Kishimoto et al. . |
| 4,791,570 | 12/1988 | Sherman et al. . |
| 4,853,682 | 8/1989 | Asano et al. . |
| 4,871,258 | 10/1989 | Herpichboehm et al. . |
| 4,882,704 | 11/1989 | Komori et al. . |
| 4,882,705 | 11/1989 | Yasue . |
| 4,890,832 | 1/1990 | Komaki . |
| 4,934,817 | 6/1990 | Gassenhuber . |
| 5,019,974 | 5/1991 | Beckers . |
| 5,037,614 | 8/1991 | Makita et al. . |
| 5,039,615 | 8/1991 | Takahata . |
| 5,047,351 | 9/1991 | Makiuchi et al. . |
| 5,053,199 | 10/1991 | Keiser et al. . |
| 5,055,261 | 10/1991 | Khoja et al. . |
| 5,059,394 | 10/1991 | Phillips et al. . |
| 5,110,226 | 5/1992 | Sherman et al. . |
| 5,153,416 | 10/1992 | Neeley . |
| 5,239,295 | 8/1993 | DeLuca et al. ............ 340/825.44 |

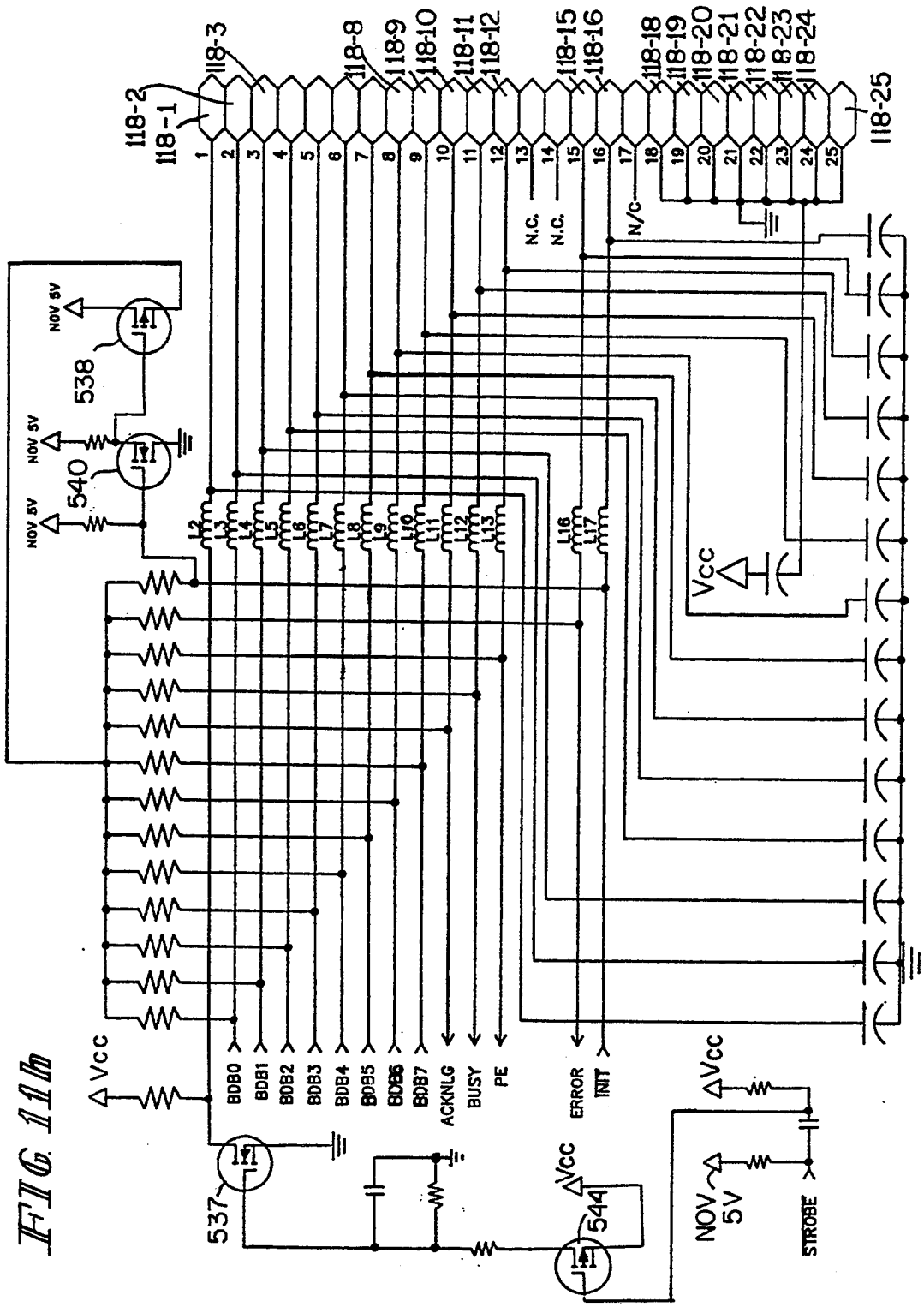

GLUCOSE TEST DATA ACQUISITION AND MANAGEMENT SYSTEM

This invention relates to methods and apparatus for adapting instruments to a common protocol for communication with, for example, a data gathering and processing system. The invention is disclosed in the context of glucose monitoring instruments, but it is believed to be useful in other applications as well.

Test strip-reading, glucose monitoring instruments of various types are in common use today. There are, for example, the ACCUTREND, ACCU-CHEK II, ACCU-CHEK III and ACCU-CHEK EASY instruments, all available from Boehringer Mannheim Corporation, 9115 Hague Road, Indianapolis, Indiana 46250-0528. There are also the instruments described in U.S. Pat. Nos.: 4,685,059; 4,168,469; 4,747,060; 4,751,648; 4,791,570; 4,882,704; 4,882,705; 4,902,948; 3,907,503; 3,980,437; 4,160,646; 4,509,859; 4,676,653; 4,871,258; 4,934,817; 5,037,614; 5,039,615; 5,053,199; 5,059,394; 5,055,261; 5,047,351; 4,791,461; 4,309,112; 3,989,383; 3,881,992; and, 4,093,849; European Published Patent Application EP 387,630 A2; Japanese Published Patent Applications: 63-269,046 and 63-61,147; German Published Patent Application 2,319,465; Diabetes, Vol. 33, Supplement 1, issued May 1984, D. Michaels et al., "A MEMORY-GLUCOSE REFLECTANCE METER FOR AUTOMATIC DATA RECORDING," entry 498, pg. 103A; Diabetes, Vol. 33, Supplement 1, issued May 1984, J. Silverstein et al., "COMPARISON OF SYSTEMS FOR BLOOD GLUCOSE MONITORING WITH A METER: ACCU-CHEK AND GLUCOMETER," entry 502 pg. 131A; Diabetes, Vol. 33, Supplement 1, issued May 1984, D. Hiennen et al., "ASSESSMENT OF ACCURACY OF 11 GLUCOSE MACHINES FOR HOME USE," entry 503 pg. 131A; and Diabetes, Vol. 33, Supplement 1, issued May 1984, V. G. Kuykendall et al., "INFORMATION MANAGEMENT FOR GLUCOMETER REFLECTANCE PHOTOMETER WITH MEMORY," entry 507, pg. 132A.

U.S. Pat. No. 5,153,416, discloses a portable, microcomputer-controlled device including a bar code reader for reading a patient's I.D. bracelet bar code and printing out labels for specimen bottles including the patient's I.D., the test(s) to be performed on the specimen, the time, the date, and the like. U.S. Pat. Nos. 4,118,687 and 4,121,574 also disclose bar code readers for use in this environment. U.S. Pat. No. 3,872,448 discloses a hospital data management system. U.S. Pat. No. 4,715,385 discloses a patient monitoring system with a detachable monitor signal processing section which can be plugged into mobile or stationary displays to drive them. U.S. Pat. Nos.: 4,890,832; 4,523,297; and, 4,853,682 all disclose systems which have a common component, such as a base, and several special components adaptable to the base. U.S. Pat. No. 4,571,702 discloses a zero power remote program storage and retrieval system. U.S. Pat. No. 5,110,226 discloses a system which communicates with an external computer. U.S. Pat. Nos. 4,731,726 and 5,019,974 disclose diabetes management systems. U.S. Pat. Nos.: 4,519,398; 4,546,436; and 4,779,199 all disclose patient monitors.

Many health care providers, such as hospitals, have substantial numbers of glucose measuring instruments of various different types with which numbers of glucose measurements are made on numbers of patients each day. Typically, the instruments have been acquired by the health care provider at different times, and so different types of instruments are used routinely. It is generally desirable to keep patient glucose readings and related data over extended periods of time, to be able to perform certain calculations, such as statistical studies, on that data, and to print hard copies of the raw data, calculation results and so on. Frequently, the glucose measuring instruments themselves are not equipped to connect to, for example, printers to provide hard copies. Similarly, the glucose measuring instruments themselves may not have the capacities to store large numbers of patient glucose readings or to perform the desired calculations, even on the small numbers of readings they are equipped to store.

An instrument according to the invention has the capability to: (1) interface with a printer for printing quality control reports, patient records and the like; (2) store larger numbers of patient glucose readings and related data than glucose measuring instruments typically are capable of storing; (3) perform various calculations on the data; (4) interface both to a number of different types of glucose measuring instruments and to a "notebook"-type computer which is capable of even greater data storage and calculation capability than the instrument of the invention itself; and, (5) provide a system lockout if quality control results of the unit are out of range.

According to one aspect of the invention, a system is provided for adapting one of a number of different types of instruments to a common protocol. Each instrument has a first serial input-output (I/O) port, first means for controlling the serial I/O port, and second means for furnishing operating power to the instrument. The system includes a type of housing for each different type of instrument. Each type of housing includes means defining openings through which selected controls and displays of a respective one of the instruments are accessible. Each housing includes third means for coupling to a respective type of instrument's first serial I/O port and fourth means for coupling to a respective type of instrument's second means.

Illustratively, according to this aspect of the invention, the second means comprises a battery enclosure having first and second battery terminals. The fourth means comprises a battery emulator having third and fourth terminals for engagement by the first and second battery terminals, respectively, when an instrument of the respective type is housed in a housing of the respective type. Fifth means couple the third and fourth terminals across a source of operating power for the respective instrument.

Further illustratively according to this aspect of the invention, the openings include an opening for an on-/off control for a respective instrument, an opening for a prompt/test results display for the respective instrument, and an opening for the insertion of unreacted/reacted test strips for the respective instrument. Illustratively, the openings further include an opening through which access to a timer control for a respective instrument can be achieved.

Additionally illustratively according to this aspect of the invention, the third means comprises a first microprocessor. Sixth means are provided for conditioning the signals at the first I/O port. Seventh means are provided for coupling the first I/O port to the sixth means. Eighth means are provided for coupling the sixth means to the first microprocessor.

Further illustratively according to this aspect of the invention, the system also includes a data processing module. The data processing module includes a first multiple conductor connector. Each type of housing includes a complementary second multiple conductor connector for connecting to the first multiple conductor connector when a respective housing is mated to the data processing module.

Illustratively according to this aspect of the invention, the data processing module further comprises first slide members. Each type of housing further comprises complementary second slide members for engagement with the first slide members when a respective housing engages the data processing module.

Illustratively according to this aspect of the invention, the data processing module further comprises a data processing module power supply. Ninth means couple the power supply across a pair of conductors of the firs multiple conductor connector. Mating of a respective housing to the data processing module connects that respective housing, its respective first microprocessor, and a respective instrument housed in that respective housing to the data processing module power supply.

Illustratively according to this aspect of the invention, the data processing module further comprises tenth means for coupling the data processing module to an external power supply, and eleventh means for coupling the external power supply across a pair of conductors of the first multiple conductor connector. Mating of a respective housing to the data processing module connects that respective housing, its respective first microprocessor, and a respective instrument housed in that respective housing to the external power supply.

Additionally illustratively according to this aspect of the invention, the data processing module further comprises a second microprocessor having a second microprocessor I/O. Twelfth means couple respective conductors of the first multiple conductor connector across a first group of pins of the second microprocessor's I/O. Thirteenth means couple a second group of pins of the second microprocessor I/O to respective terminals of the second serial I/O port.

Further illustratively according to this aspect of the invention, the thirteenth means comprises an RS232-to-transistor-transistor logic (TTL)/TTL-to-RS232 interface.

Additionally illustratively according to this aspect of the invention, the thirteenth means comprises an optical isolator. A receive data terminal of the second serial I/O port is coupled to a light source portion of the optical isolator. Fourteenth means couple a light activated switch portion of the optical isolator to an RS232-to-TTL received data output terminal of the RS232-to-TTL/TTL-to-RS232 interface.

According to this aspect of the invention, the fourteenth means comprises an interrupt pin of the second microprocessor I/O.

Additionally according to this aspect of the invention, fifteenth means switches power to the RS232-to-TTL/TTL-to-RS232 interface. The fifteenth means is coupled to the second means, to an operating power supply terminal of the RS232-to-TTL/TTL-to-RS232 interface, and to the interrupt pin of the second microprocessor I/O. Receipt of data on the receive data terminal of the second serial I/O port causes power to be supplied from the second means to the operating power supply terminal of the RS232-to-TTL/TTL-to-RS232 interface to activate the RS232-to-TTL/TTL-to-RS232 interface and to activate a switch in the RS232-to-TTL output terminal of the RS232-to-TTL/TTL-to-RS232 interface.

According to another aspect of the invention, a zero-power receive detector is provided for a serial data interface including a receive data terminal, a received serial data out terminal and an operating power supply terminal. The detector comprises first means for furnishing operating power to the interface, and second means for switching power to the interface. The second means is coupled between the first means and the operating power supply terminal of the interface. Third means are provided for coupling a light source portion of an optical isolator to the receive data terminal. Fourth means couple a light activated switch portion of the optical isolator to the second means.

Illustratively, according to this aspect of the invention, the fourth means latches the second means in its state in which power is supplied from the first means to the operating power supply terminal.

Further illustratively according to this aspect of the invention, the fourth means disables the second means from responding to further signals from the light activated switch portion of the optical isolator.

Additionally illustratively according to this aspect of the invention, fifth means switches the serial data out line to the received serial data out terminal. The fifth means is coupled between the received serial data out terminal and the received serial data out line. Illustratively, the fourth means switches the second means. Further illustratively, the fourth means comprises a microprocessor.

The invention may best be understood by referring to the following description and accompanying drawings which illustrate the invention. In the drawings:

FIG. 5a illustrates an enlarged fragmentary sectional view of a detail of FIG. 5, taken generally along section lines 5a—5a of FIG. 5;

FIG. 8 illustrates in partly block and partly schematic form a circuit contained within the housing of FIG. 7;

Figure 1:
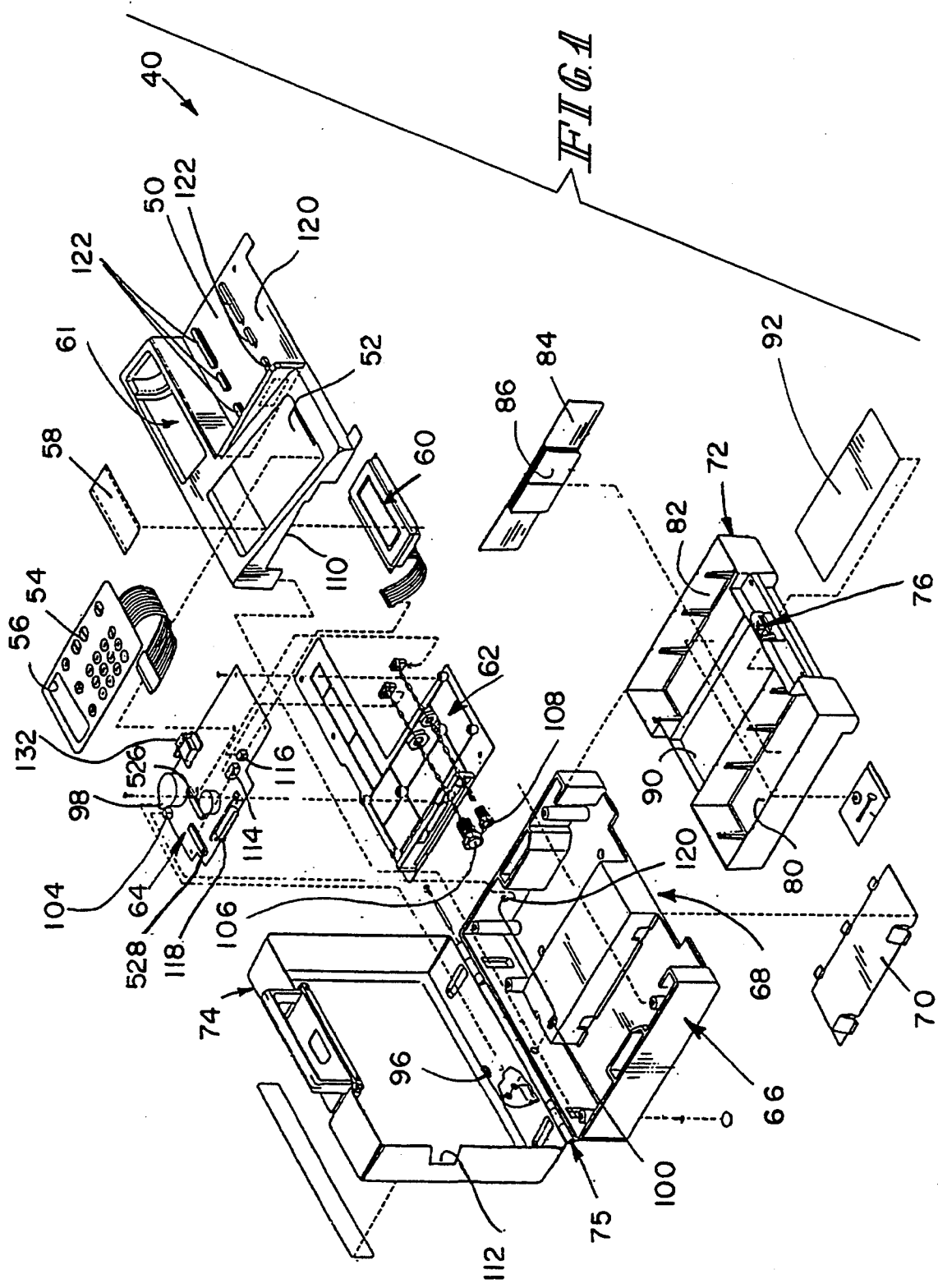
FIG. 1 illustrates an exploded perspective view of an instrument constructed according to the invention.

FIG. 1 illustrates an exploded perspective view of a remote glucose test station (GTS) 40 for incorporating a selected one of a number of different glucose meters, illustratively, the Boehringer Mannheim Corporation ACCU-CHEK II 42, ACCU-CHEK III 44, ACCU-CHEK EASY 46, and ACCUTREND 48 meters. The GTS 40 includes provisions for storing data, such as date, time, glucose reading and a patient identifier, related to a number of glucose readings from each of a number of patients taken from the meter 42, 44, 46 or 48 incorporated into it, for providing this information in (a) suitable (formats) to a printer (not shown) coupled to a printer port on the GTS 40, and/or for supplying this information in such format(s) to a hospital data management (HDM) system (not shown) through a port provided for such communication on GTS 40. A suitable printer is one which is supported by the IBM/Epson standard. A suitable HDM system would be, for example, Digital Equipment Corporation's DEC320P (Model PCP11) notebook computer. GTS 40 also includes a bar code reader port for coupling a bar code reader (not shown), such as, for example, a Welch Allyn Model 6180/A-25999247 bar code reader, to GTS 40.

GTS 40 includes a top 50 with a relief 52 for a keypad 54. Keypad 54 is provided with an opening 56 covered by a lens 58 through which a display 60 is visible. A well 61 is provided in top 50 for, for example, a vial of unreacted blood glucose measurement strips. A midplate 62 on which are mounted the main GTS printed circuit board (PCB) 64 and other GTS hardware is captured between top 50 and GTS base 66 by appropriate threaded fasteners which extend upward through base 66 and midplate 62 and into top 50. PCB 64 is mounted to midplate 62 by appropriate threaded fasteners. Base 66 is provided with a central battery well 68 which houses, for example, six "C" cells (not shown) which are inserted into the well 68 from the underside of base 66. A battery well cover 70 snaps into closing orientation to close well 68.

A storage drawer 72 is slidable between base 66 and midplate 62. A cover 74 is hinged 75 at the rear of base 66. Drawer 72 is prevented from inadvertently sliding out of base 66 and cover 74 is prevented from inadvertently opening when cover 74 is closed by engagement of a tab 76 on the front of drawer 72 in an opening 78 on the front of cover 74. Drawer 72 is provided with left and right storage compartments 80, 82, respectively, each of which can accept longitudinal 84 or transverse 86 dividers for dividing the compartment 80, 82 into smaller compartments. These compartments are convenient for holding bandages, antiseptic swabs, and other equipment necessary for the taking of, for example, blood samples from the pricked fingers of diabetes sufferers for measurement by a glucose meter 42, 44, 46 or 48 incorporated into GTS 40 in a manner to be described.

The central area 90 of drawer 72 is provided with a "comments code" chart 92 which desirably contains comments to patient record data encoded into bar code. In operation, a health care provider may wish to add comments to patient record data after a reading is taken for storage in the GTS 40. The health care provider can pick the correct code from chart 92, pass the bar code reader over the bar code accompanying that comment and have that comment entered with the patient record data. A connector 96 and associated insulated conductors supply power from the battery well 68 to the battery power socket 98 on PCB 64. Alternatively, power can be supplied from an external low voltage DC source through a socket 100 accessible through the rear of base 66 and associated insulated conductors to a connector 102 and external DC supply socket 104 provided on PCB 64. A bar code reader port 106 is accessible with cover 74 closed or open by virtue of notches 110, 112 in the lower left-hand side edges of top 50 and cover 74, respectively. Appropriate insulated conductors and connectors extend from port 106 and a serial I/O (RS232) port 108 to sockets 114, 116 provided on PCB 64 for entry and serial I/O, respectively. A printer port 118 mounted on PCB 64 is accessible with cover 74 open by virtue of notch 110.

Figure 2:
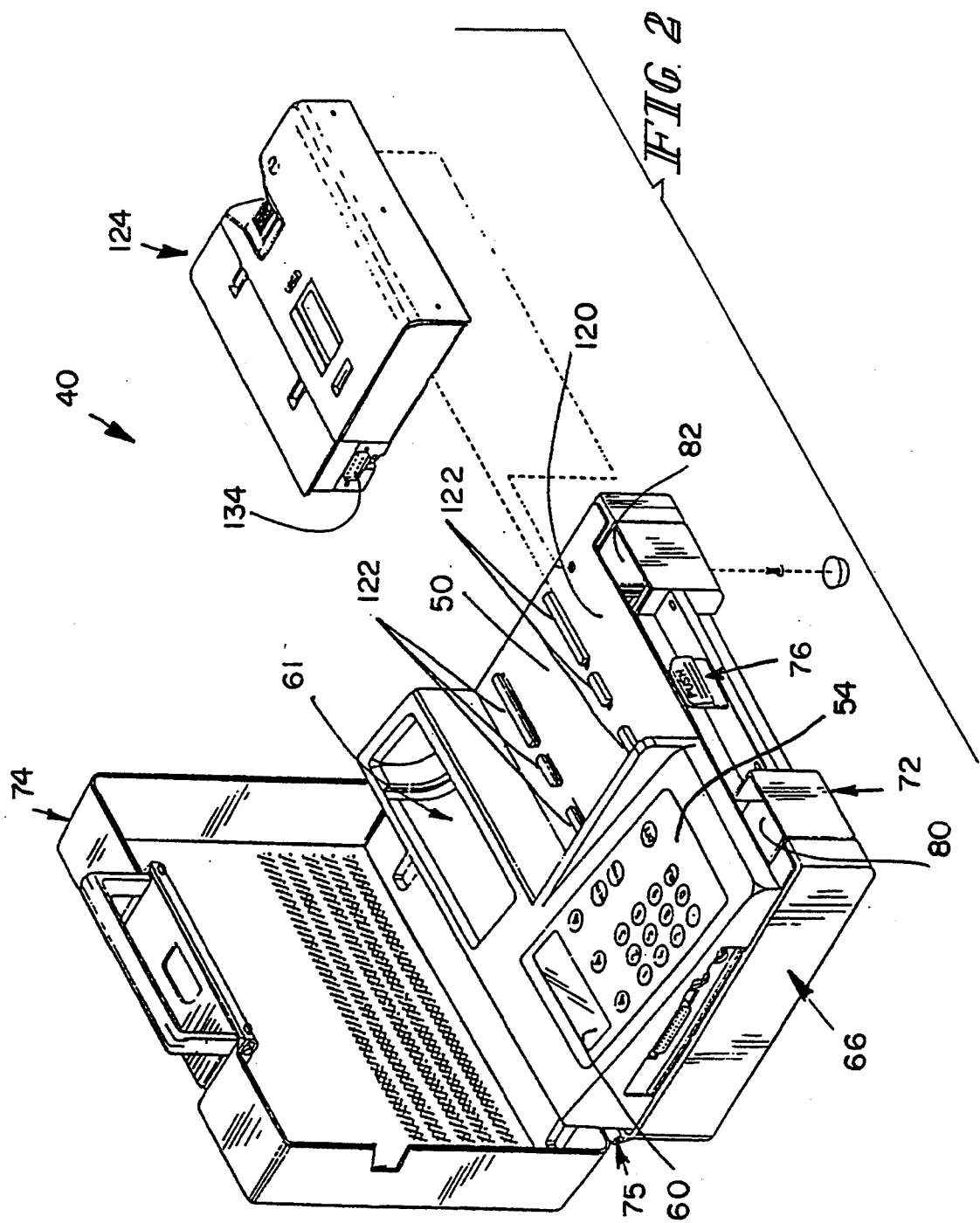
FIG. 2 illustrates a perspective view of the instrument of FIG. 1 assembled, with a housing containing instrument of Figs capable of interfacing removed one of the glucose measuring instruments with which the from it.

The front right-hand side area 120 of top 50 is generally flat and provided with a pair of parallel, somewhat inverted L-shaped transverse section slides 122. As best illustrated in FIG. 2, these slides 122 permit one of four housings 124 (FIGS. 2–3), 126 (FIG. 5), 128 (FIG. 7), 130 (FIG. 9), each provided with a complementary pair of parallel slides 125, 127, 129, 131, respectively, to be slid from the right onto slides 122 until the respective housing 124, 126, 128, 130 occupies area 120. An appropriate threaded fastener can then be inserted through the base 66 into an opening (not shown) provided therefor in the bottom of housing 124, 126, 128, 130 to lock housing 124, 126, 128, 130 onto GTS 40. A nine-pin connector 132 provided on PCB 64 engages a complementary connector socket 134, 234, 334, 434 associated with the respective housing 124, 126, 128, 1313 when the housing 124, 126, 128, 130 is slid fully into position on GTS 40. All of the required electrical connections between the meter in housing 124, 126, 128 or 130 and the remaining electronics of GTS 40 are made by this act.

Figure 3:
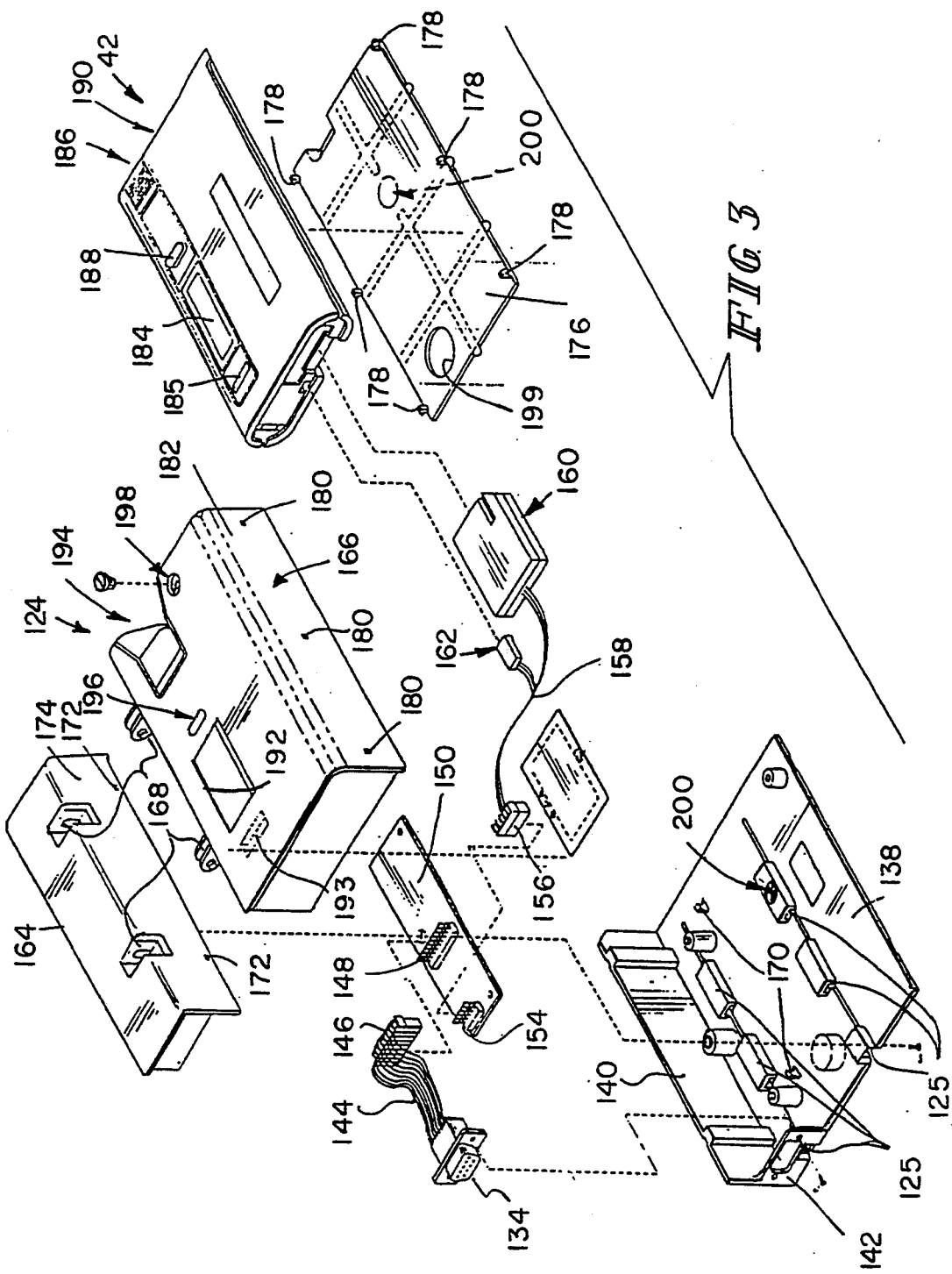
FIG. 3 illustrates the glucose measuring instrument of FIG. 2 and its housing in exploded perspective.

Housing 124 and its contents are better illustrated in FIG. 3, an exploded perspective view of these components. The illustrated meter 42 is a Boehringer Mannheim Corporation ACCU-CHEK II blood glucose meter. Housing 124 includes a housing bottom 138 provided with the previously mentioned slides 125 and a back 140 which extends generally perpendicularly to bottom 138. A wall 142 extends forward from back 140 along the left edge of bottom 138 to mount the connector socket 134. An insulated multiple conductor cable 144 extends from socket 134 to complementary connectors 146, 148 provided on a printed wiring board (PWB) 150 on which is mounted an adaptive communications processor (ACP) 152, illustrated in partly block and partly schematic circuit form in FIG. 4. The PWB 150 is mounted to bottom 138 at the rear thereof, adjacent back 140, by appropriate threaded fasteners. The meter 42 is connected electrically to the circuitry on PWB 150 by a complementary connector 154 and socket 156. Connector 154 is mounted on PWB 150. Socket 156 is provided on one end of an insulated multiple conductor cable 158, the conductors of which are split into two groups intermediate the ends of cable 158 and provided with separate adaptor sockets 160 and 162 to supply power to the meter 42 and a connection to the meter 42's serial I/O port, respectively.

The housing 124 top is divided into a rear portion 164 and a front portion 166 which are hinged 168 together. The rear top portion 164 is secured to the bottom 138 by a suitable threaded fastener, which simultaneously captures PWB 150 between rear top portion 164 and bottom 138, and by resilient pawl-like fasteners 170 provided on bottom 138 which snap into openings 172 provided therefor on a front wall 174 of rear top portion 164. The meter 42 is held in position within housing 124 by a mount 176 provided along its front and rear edges with resilient, pawl-like fasteners 178 which engage openings 180 provided therefor in front and rear walls 182 of front top portion 166. Resilient snapping engagement of fasteners 178 into openings 180 captures meter 42 against the underside of front top portion 166 and presents the user interface of meter 42 (that is, its display 184, calibrate bar code reader 185, reacted test strip slot 186, timer button 188, and ON/OFF button 190) at appropriate locations 192, 193, 194, 196, 198 on front top portion 166. Small VELCRO synthetic hook-and-eyelet material circles 200 provided on bottom 138 and the underside of mount 176 normally maintain front top portion 166 in a closed orientation. The hinged 168 mounting of front top portion 166 to rear top portion 164, the VELCRO fasteners 200, and an opening 199 provided in mount 176 permit front top portion 166 to be raised and the bar code calibration strip for a vial of unreacted glucose measurement strips to be fed into calibrate bar code reader 185 and retrieved as it passes out of opening 199.

The following schematic and block circuit diagram descriptions identify specific integrated circuits and other components and in many cases specific sources for these. Specific terminal and pin names and numbers are generally given in connection with these for the purposes of completeness. It is to be understood that these terminal and pin identifiers are provided for these specifically identified components. It is to be understood that this does not constitute a representation, nor should any such representation be inferred, that the specific components or sources are the only components available from the same or any other sources capable of performing the necessary functions. It is further to be understood that other suitable components available from the same or different sources may not use the same terminal/pin identifiers as those provided in this description.

Figure 4:
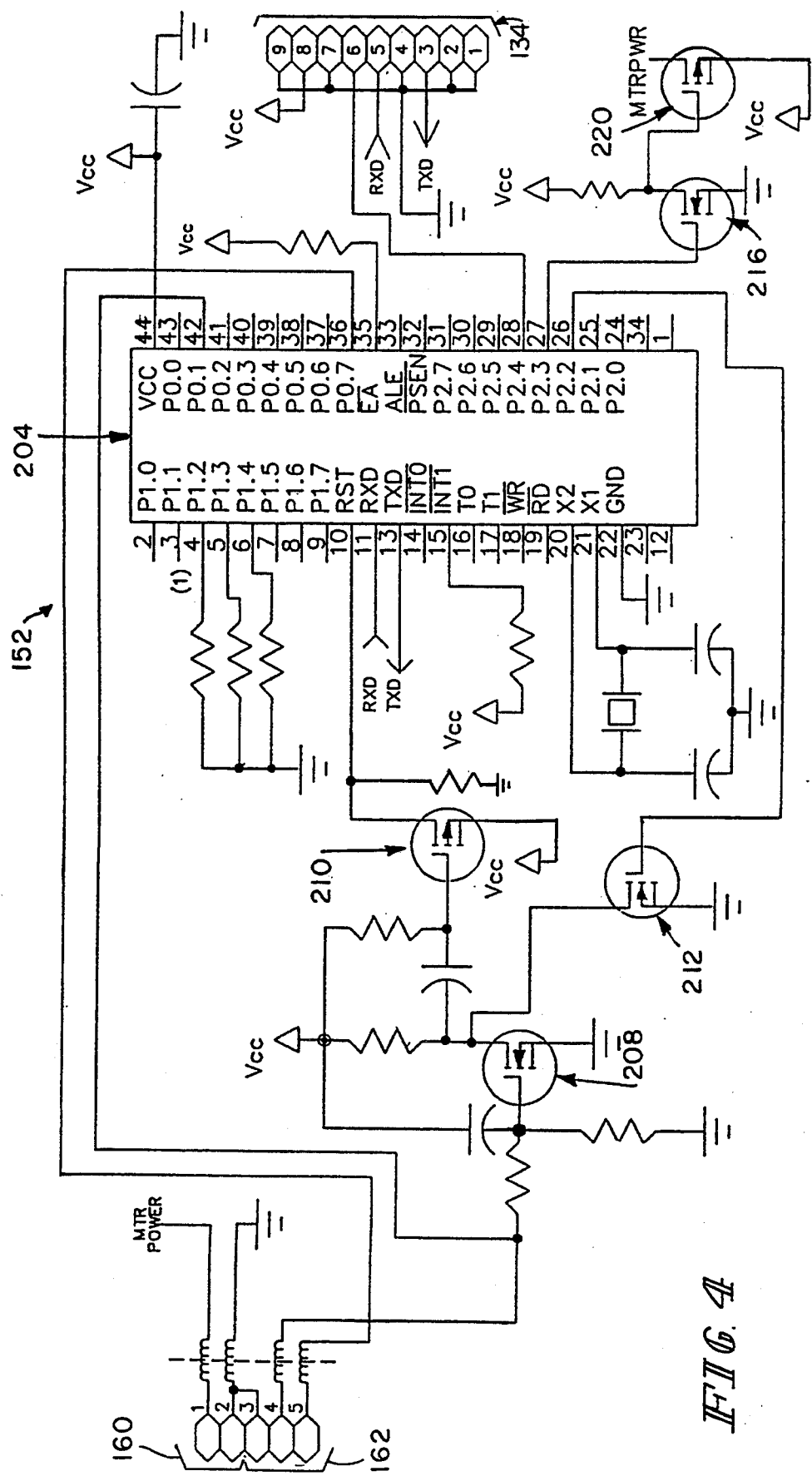
FIG. 4 illustrates in partly block and partly schematic form a circuit contained within the housing of FIG. 3.

Turning now to FIG. 4, meter 42 is powered by a MeTeRPoWeR potential supply maintained across the two conductors, pins 1 and 2, associated with socket 160. One of these conductors is also the ACP 152 ground. Meter 42 I/O is provided through the three conductors associated with socket 162. The ACP 152 associated with meter 42 includes an Intel 80C51 microprocessor ($\mu$P) 204 mounted on PWB 150. The nine pin receptacles of socket 134 are coupled as follows: pin receptacles 1, 2, 4, 7 and 9 to system ground; pin receptacle 3 is the transmit data (TXD) terminal of ACP 152; pin receptacle 5 is the receive data (RXD) terminal of ACP 152; pin receptacle 6 is coupled to the P2.4 terminal of P 204; and, pin receptacle 8 is coupled to the $V_{cc}$ supply. Pin 3 of socket 162 is coupled to pin 2 of socket 160. The ungrounded terminals, pins 4 and 5, of socket 162 are coupled through respective inductors of a common mode (wound on a common core) ESD/EMI protector to terminals P0.1 and P0.7, respectively, of $\mu$P 204 The TXD and RXD terminals, receptacles 3 and 5, respectively, of socket 134 are coupled to the TXD and RXD terminals, respectively, of $\mu$P 204.

Terminal P0.1 of $\mu$P 204 is also coupled through a 100 K resistor to the gate electrode of a Siemens type BSS138 field effect transistor (FET) 208. The gate of FET 208 is coupled to $V_{cc}$ through a 0.47 $\mu$F capacitor and to ground through a 1M resistor. The source of FET 208 is coupled to ground. Its drain is coupled through a 100 K resistor to $V_{cc}$, through a 0.47 $\mu$F capacitor to the gate of a Siemens type BSS84 FET 210 and directly to the drain of a type BSS138 FET 212 The gate of FET 210 is coupled to $V_{cc}$ through a 100 K resistor The source of FET 212 is coupled to ground. The gate of FET 212 is coupled to the P2.2 terminal of $\mu$P 204. The source of FET 210 is coupled to $V_{cc}$. The drain of FET 210 is coupled to the RST terminal of $\mu$P 204 and to ground through a 4.75 K resistor. The INT1 and $\overline{EA}$ terminals of $\mu$P 204 are coupled through respective 1 K resistors to $V_{cc}$. The $V_{cc}$ terminal of $\mu$P 204 is coupled to $V_{cc}$ and through a 0.1 $\mu$F capacitor to ground. The GND terminal of $\mu$P 204 is coupled to ground. The P1.2, P1.3 and P1.4 terminals of $\mu$P 204 are coupled through respective 100 $\Omega$ "personality" resistors, which match the characteristics of meter 42 to ACP 152, to ground. The P2.3 terminal of $\mu$P 204 is coupled to the gate of a type BSS138 FET 216. The source of FET 216 is grounded. The drain of FET 216 is coupled through a 1M resistor to $V_{cc}$ and directly to the gate of a Samsung type IRFR9020 FET 220. The source of FET 216 is coupled to ground. The source of FET 220 is coupled to $V_{cc}$. The drain of FET 220 is coupled to the MeTeRPoWeR terminal. A time base for ACP 152 is provided by a 1.8432 MHz crystal coupled across terminals X1–X2 of $\mu$P 204. Each of terminals X1 and X2 of $\mu$P204 is also coupled to ground through a respective 33 pF capacitor.

Figure 5:
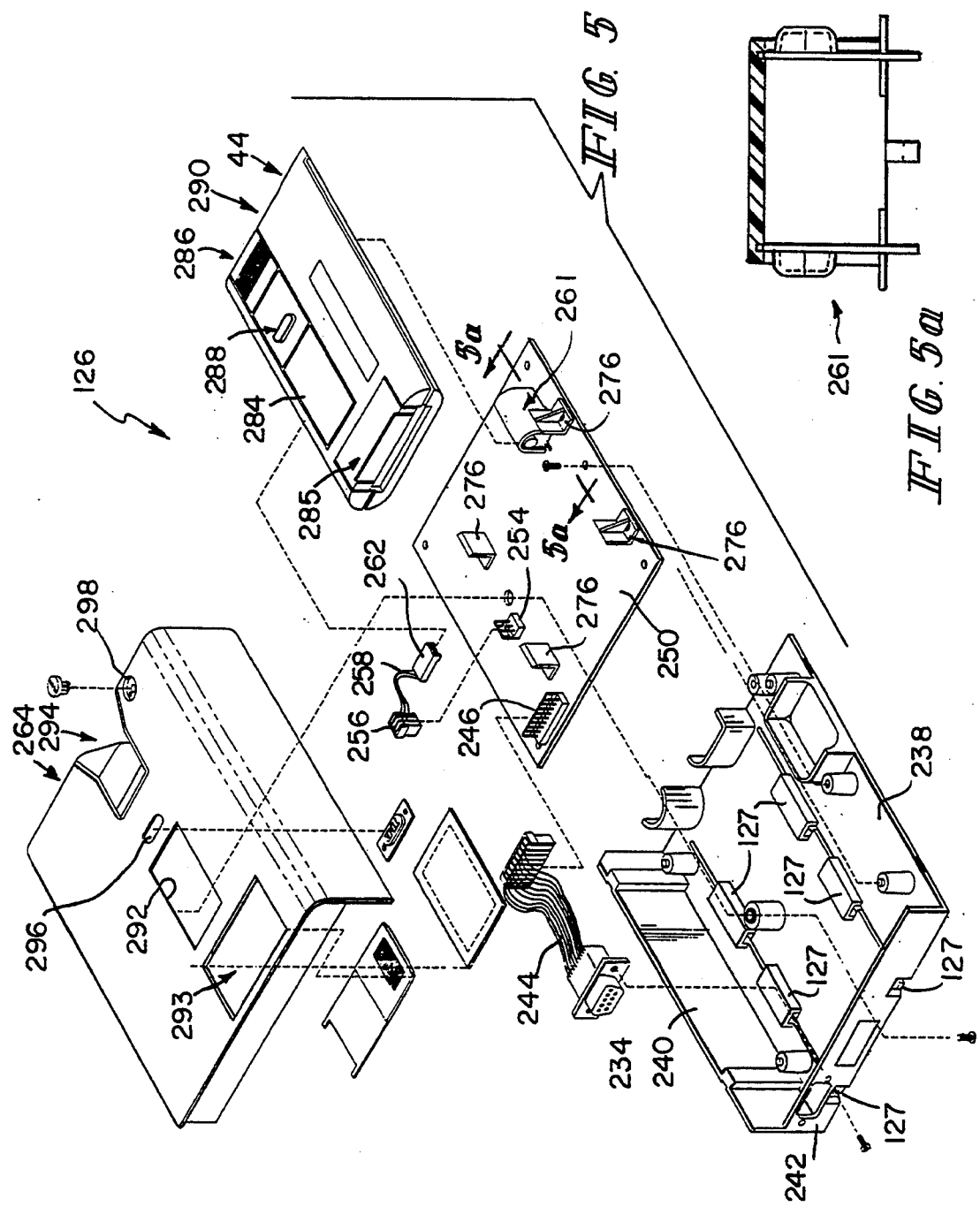
FIG. 5 illustrates another glucose measuring instrument with which the instrument of FIG. 1 is capable of interfacing, and the housing for that glucose measuring instrument in exploded perspective.

Housing 126 and its contents are better illustrated in FIG. 5, an exploded perspective view of these components. The illustrated meter 44 is a Boehringer Mannheim Corporation ACCU-CHEK III blood glucose meter. Housing 126 includes a housing bottom 238 provided with the previously mentioned slides 127 and a back 240 which extends generally perpendicularly to bottom 238. A wall 242 extends forward from back 240 along the left edge of bottom 238 to mount connector socket 234. An insulated multiple conductor cable 244 extends from socket 234 to connector 246 provided on a PWB 250 on which is mounted an ACP 252, illustrated in partly block and partly schematic circuit form in FIG. The PWB 250 is mounted to bottom 238 by appropriate threaded fasteners.

The meter 44 is connected electrically to the circuitry on PWB 250 by a complementary connector 254 and socket 256. Connector 254 is mounted on PWB 250. Socket 256 is provided on one end of an insulated multiple conductor cable 258, the other end of which is provided with a plug 262 for connecting to the serial I/O port socket of meter 44. Meter 44 is also coupled to the circuit on PWB 250 by a battery emulator 261 which fits into the battery well of meter 44 when the battery well door and batteries are removed therefrom. The general configuration of battery emulator 261 can best be appreciated by referring to FIG. 5a which is a fragmentary sectional view taken generally along section lines 5a—5a of FIG. 5. Power to operate the meter 44 is supplied from the circuitry on PWB250, best illustrated in FIG. 6, through emulator 261 to the meter 44 to operate it. The housing 126 top portion 264 is secured to the bottom 238 by a suitable threaded fastener. The meter 44 is held in position within housing 126 by four meter locating tabs 276 provided on PWB250, by battery emulator 261, and by being captured between the assembled PWB250 and top 264 of housing 126. This arrangement presents the user interface of meter 44 (that is, its display 284, calibrate bar code reader 285, reacted test strip slot 286, timer button 288, and ON/-OFF button 290) at appropriate locations 292, 293, 294, 296, 298 on top 264.

Figure 6:
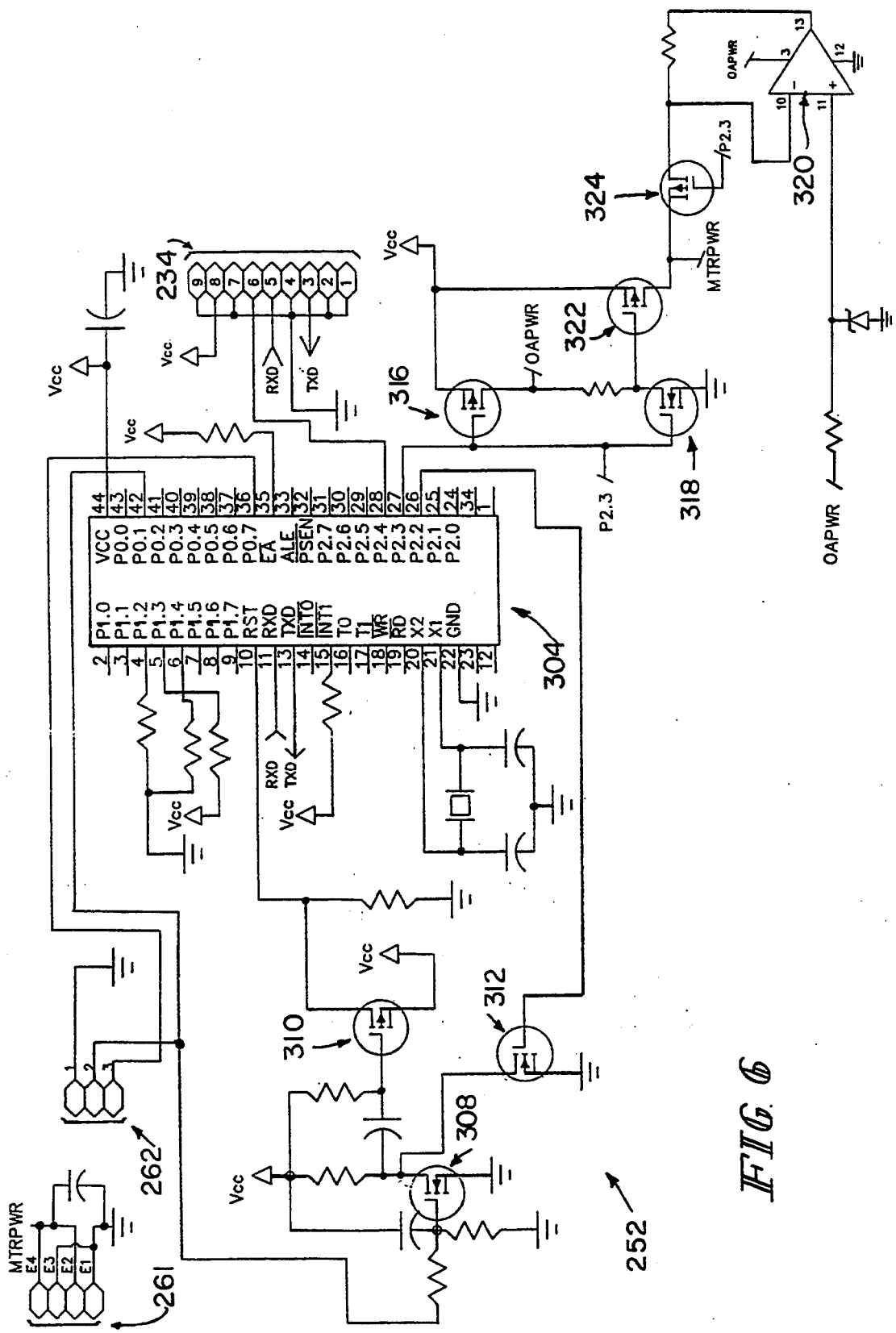

Turning now to FIG. 6, meter 44 is powered by a MeTeRPoWeR potential supply maintained across the two pairs of conductors, pins E2, E4 and E1, E3 associated with battery emulator 261. One pair, E1, E3, of these conductors is also the ACP 252 ground. A 0.001 $\mu$F capacitor is coupled between E2, E4 and E1, E3. Meter 44 I/O is provided through the three conductors associated with socket 262 The ACP 252 associated with meter 44 includes an Intel 80C51 $\mu$P 304 mounted on PWB 250. The nine pin receptacles on socket 234 are coupled as follows: pin receptacles 1, 2, 4, 7 and 9 to system ground; pin receptacle 3 is the TXD terminal of ACP 252; pin receptacle 5 is the RXD terminal of ACP 252; pin receptacle 6 is coupled to the P2.4 terminal of $\mu$P 304; and, pin receptacle 8 is coupled to the $V_{cc}$ supply.

Pin 1 of socket 262 is coupled to the system ground. Pins 2 and 3 of socket 262 are coupled to the P0.1 and P0.7 terminals, respectively, of $\mu$P 304. The TXD and RXD terminals, receptacles 3 and 5, respectively, of socket 234 are coupled to the TXD and RXD terminals, respectively, of $\mu$P 304. Terminal P0.1 of $\mu$P 304 is also coupled through a 100 K resistor to the gate electrode of a type BSS138 FET 308. The gate of FET 308 is coupled to $V_{cc}$ through a 0.47 $\mu$F capacitor and to ground through a 1M resistor. The source of FET 308 is grounded. The drain of FET 308 is coupled through a 100 K resistor to $V_{cc}$, through a 047 $\mu$F capacitor to the gate of a type BSS84 FET 310 and directly to the drain of a type BSS138 FET 312. The gate of FET 310 is coupled to $V_{cc}$ through a 100 K resistor. The source of FET 312 is coupled to ground. The gate of FET 312 is coupled to the P2.2 terminal of 304. The source of FET 310 is coupled to $V_{cc}$. The drain of FET 310 is coupled to the RST terminal of $\mu$P 304 and through a 4.75 K resistor to ground. The "and terminals of $\mu$P 304 are coupled through respective 10 K resistors to $V_{cc}$. The $V_{cc}$ terminal of $\mu$P 304 is coupled to $V_{cc}$ and through a 0.1 $\mu$F capacitor to ground. The GND terminal of $\mu$P 304 is coupled to ground.

The P1.2 and P1.4 terminals of $\mu$P 304 are coupled through respective 100 fi resistors to ground. The P1.3 terminal of $\mu$P 304 is coupled through a 10 K resistor to $V_{cc}$. The P2.3 terminal of $\mu$P 304 is coupled to the gate of a type BSS84 FET 316 and to the gate of a type BSS138 FET 318. The source of FET 316 is coupled to $V_{cc}$. The source of FET 318 is coupled to ground. The drain of FET 316 is coupled through a 100 fi resistor to the drain of FET 318. Operational Amplifier PoWeR for a National Semiconductor type LP339M difference amplifier 20 is supplied from the drain of FET 316. The drain of FET 318 is coupled to the gate of a type IRFR9020 FET 22. The source of FET 322 is coupled to V. The drain of FET 322 is coupled to the source of a type BSS84 FET 324. The drain of FET 324 is coupled to the inverting (−) input terminal of amplifier 320 and through a 300 Ω resistor to the output terminal of amplifier 320. The gate of FET 324 is coupled to the P2.3 terminal of $\mu$P 304. The drain of FET 322 and source of FET 324 are coupled to MeTeRPoWeR. The non-inverting (+) input terminal of amplifier 320 is coupled through a 1 K resistor to OAPWR and to the cathode of a type 1N5225B zener diode, the anode of which is grounded. A time base for ACP 252 is provided by a 1.8432 MHz crystal coupled across terminals X1-X2 of $\mu$P 304. Each of terminals X1 and X2 of $\mu$P 304 is also coupled to ground through a respective 33 pF capacitor.

Figure 7:
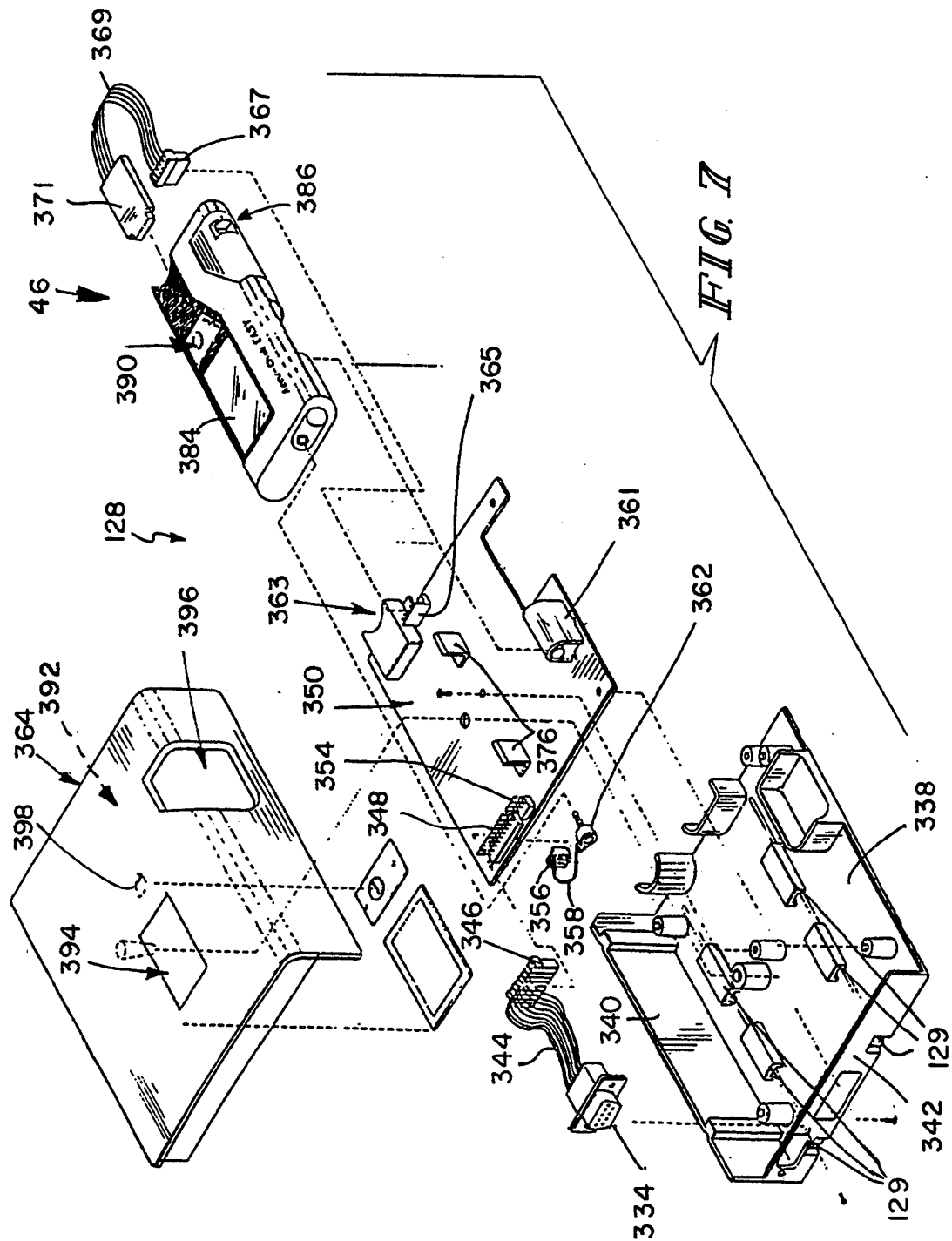
FIG. 7 illustrates another glucose measuring instrument with which the instrument of FIG. 1 is capable of interfacing, and the housing for that glucose measuring instrument in exploded perspective.

Housing 128 and its contents are better illustrated in FIG. 7, an exploded perspective view of these components. The illustrated meter 46 is a Boehringer Mannheim Corporation ACCU-CHEK EASY blood glucose meter. Housing 128 includes a housing bottom 338 provided with the previously mentioned slides 129 and a back 340 which extends generally perpendicularly to bottom 338. A wall 342 extends forward from back 340 along the left edge of bottom 338 to mount the connector socket 334. An insulated multiple conductor cable 344 extends from socket 334 to complementary connectors 346, 348 provided on a PWB 350 on which is mounted an ACP 352, illustrated in partly block and partly schematic circuit form in FIG. 8. The PWB 350 is mounted to bottom 338 by appropriate threaded fasteners. The meter 46 is connected electrically to the circuitry on PWB 350 by a complementary connector 354 and socket 356. Connector 354 is mounted on PWB 350. Socket 356 is provided on one end of an insulated multiple conductor cable 358 which is provided with a jack 362 to connect PWB350 to the meter 46's serial I/O port. A battery emulator 361 not unlike the emulator 261 of FIGS. 5 and 5a in configuration is provided on PWB350 to supply operating power to meter 46.

A ROM code key socket 363 is provided on PWB350 for the purposes discussed in U.S. Pat. No. 5,053,199. The various terminals of socket 363 are connected electrically through a plug 365 provided on PWB 350, a socket 367, an insulated multiple conductor cable 369 and a ROM code key emulator plug 371 to the ROM code key socket on meter 46. The housing 128 includes a top portion 364 secured to the bottom 338 by a suitable threaded fastener. The meter 46 is held in position within housing 128 by two meter locating tabs 376 provided on PWB350, by battery emulator 361, and by being captured between the assembled PWB350 and top 364 of housing 128. This arrangement presents the user interface of meter 46 (that is, housing 128's ROM code key socket 363, display 384, reacted test strip slot 386. and ON/OFF button 390) at appropriate locations 392, 394, 396, 398 on top portion 364.

Figure 8:
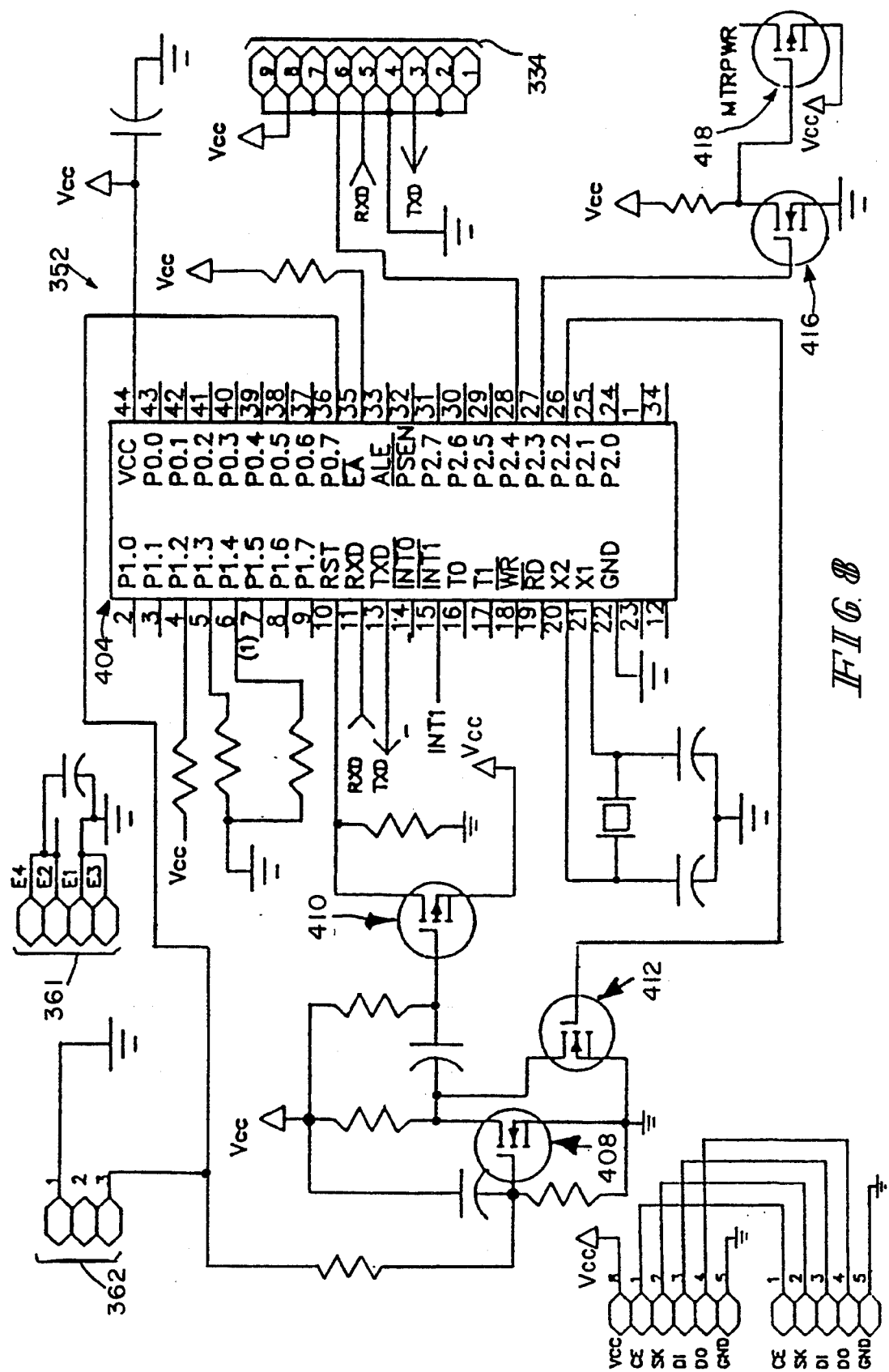
FIG. 8 illustrates in partly block and partly schematic form a circuit contained within the housing of FIG. 5.

Turning now to FIG. 8, meter 46 is powered by a MeTeRPoWeR potential supply maintained across the two pairs of conductors, pins E2, E4 and E1, E3 associated with battery emulator 361. One pair, E1, E3, of these conductors is also the ACP 352 ground. A 0.001 $\mu$F capacitor is coupled between E2, E4 and E1, E3. Meter 46 I/O is provided through the three conductors associated with socket 362. The ACP 352 associated with meter 46 includes an Intel 80C51 $\mu$P 404 mounted on PWB 350. The nine pin receptacles on socket 334 are coupled as follows: pin receptacles 1, 2, 4, 7 and 9 to system ground; pin receptacle 3 is the TXD terminal of ACP 352; pin receptacle 5 is the RXD terminal of ACP 352; pin receptacle 6 is coupled to the P2.4 terminal of $\mu$P 404; and, pin receptacle 8 is coupled to the $V_{cc}$ supply.

Pin 1 of socket 362 is coupled to the system ground. Pin 3 of socket 362 is coupled to the P0.7 terminal of μP 404. The TXD and RXD terminals, pins 3 and 5, respectively, of socket 334 are coupled to the TXD and RXD terminals, respectively, of μP 404. Terminal P0.7 of μP 404 is also coupled through a 100 K resistor to the gate electrode of a type BSS138 FET 408. The gate of FET 408 is coupled to $V_{cc}$ through a 0.47 μF capacitor and to ground through a 1M resistor. The source of FET 408 is grounded. The drain of FET 408 is coupled through a 100 K resistor to $V_{cc}$, through 0.47 μF capacitor to the gate of a type BSS84 FET 410 and directly to the drain of a type BSS138 FET 412. The gate of FET 410 is coupled to $V_{cc}$ through a 100 K resistor. The source of FET 412 is coupled to ground. The gate of FET 412 is coupled to the P2.2 terminal of μP 404 The source of FET 410 is coupled to $V_{cc}$. The drain of FET 410 is coupled to the RST terminal of μP 404 and through a 4.75 K resistor to ground. The $\overline{EA}$ terminal of μP 404 is coupled through a 10 K resistor to $V_{cc}$. The $V_{cc}$ terminal of μP 404 is coupled to $V_{cc}$ and through a 0.1 μF capacitor to ground. The GND terminal of μP 404 is coupled to ground. The P1.2 terminal of μP 404 is coupled through a 10 K resistor to $V_{cc}$. The P1.3 and P1.4 terminals of μP 404 are coupled through respective 100 Ω resistors to ground. The P2.3 terminal of μP 404 is coupled to the gate of a type BSS138 FET 416. The source of FET 416 is coupled to ground, and its drain is coupled through a 1M resistor to $V_{cc}$ and directly to the gate of a type IRFR9020 FET 418. The source of FET 418 is coupled to $V_{cc}$ and the drain of FET 418 is coupled to the MeTeRPoWeR terminal, E2, E4 associated with battery emulator 361.

Figure 9:
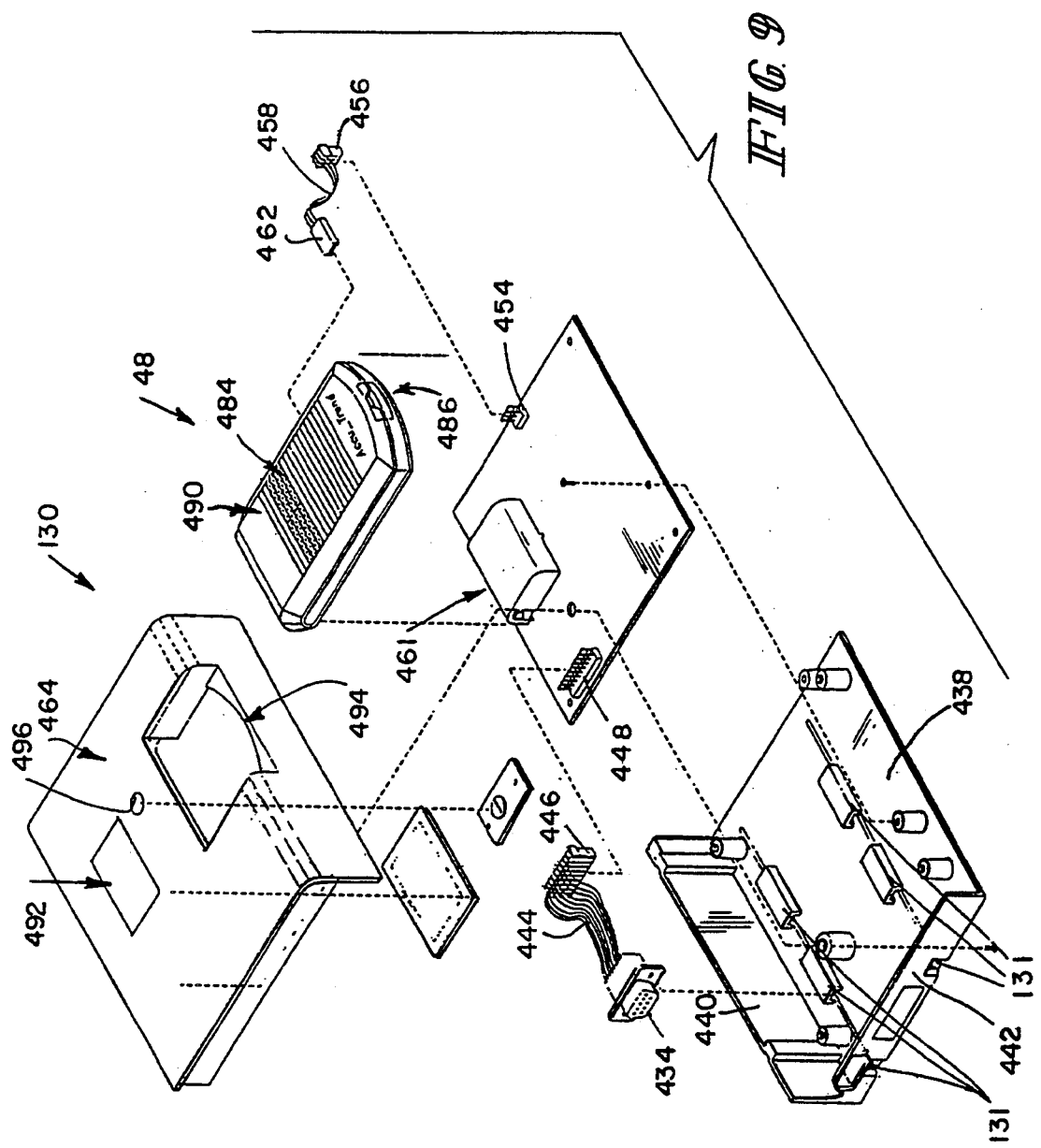
FIG. 9 illustrates another glucose measuring instrument with which the instrument of FIG. 1 is capable of interfacing, and the housing for that glucose measuring instrument in exploded perspective.

Housing 130 and its contents are better illustrated in FIG. 9, an exploded perspective view of these components. The illustrated meter 48 is a Boehringer Mannheim Corporation ACCU-TREND blood glucose meter. Housing 130 includes a housing bottom 438 provided with the previously mentioned slides 131 and a back 440 which extends generally perpendicularly to bottom 438. A wall 442 extends forward from back 440 along the left edge of bottom 438 to mount the connector socket 434. An insulated multiple conductor cable 444 extends from socket 434 to complementary connectors 446, 448 provided on a PWB 450 on which is mounted an ACP 452, illustrated in partly block and partly schematic circuit form in FIG. 10. The PWB 450 is mounted to bottom 438 at the rear thereof, adjacent back 440, by appropriate threaded fasteners. The meter 48 is connected electrically to the circuitry on PWB 450 by a complementary connector 454 and socket 456. Connector 454 is mounted on PWB 450. Socket 456 is provided on one end of an insulated multiple conductor cable 458 provided with a socket 462 to provide a connection to the meter 48's serial I/O port. A battery emulator 461, similar in configuration to battery emulators 261, 361 of FIGS. 5-5a and 7, is provided on PWB450 to supply operating power to meter 48. The housing 130 includes a top portion 464 secured to the bottom 438 by a suitable threaded fastener, which simultaneously captures PWB 450 between top 464 and bottom 438. The meter 48 is held in position within housing 130 by battery emulator 461 and by being captured between the assembled PWB450 and top 464 of housing 130. This arrangement presents the user interface of meter 48 (that is, its display 484, reacted test strip slot 486, and ON/OFF button 490) at appropriate locations 492, 494, 496 on top 464.

Figure 10:
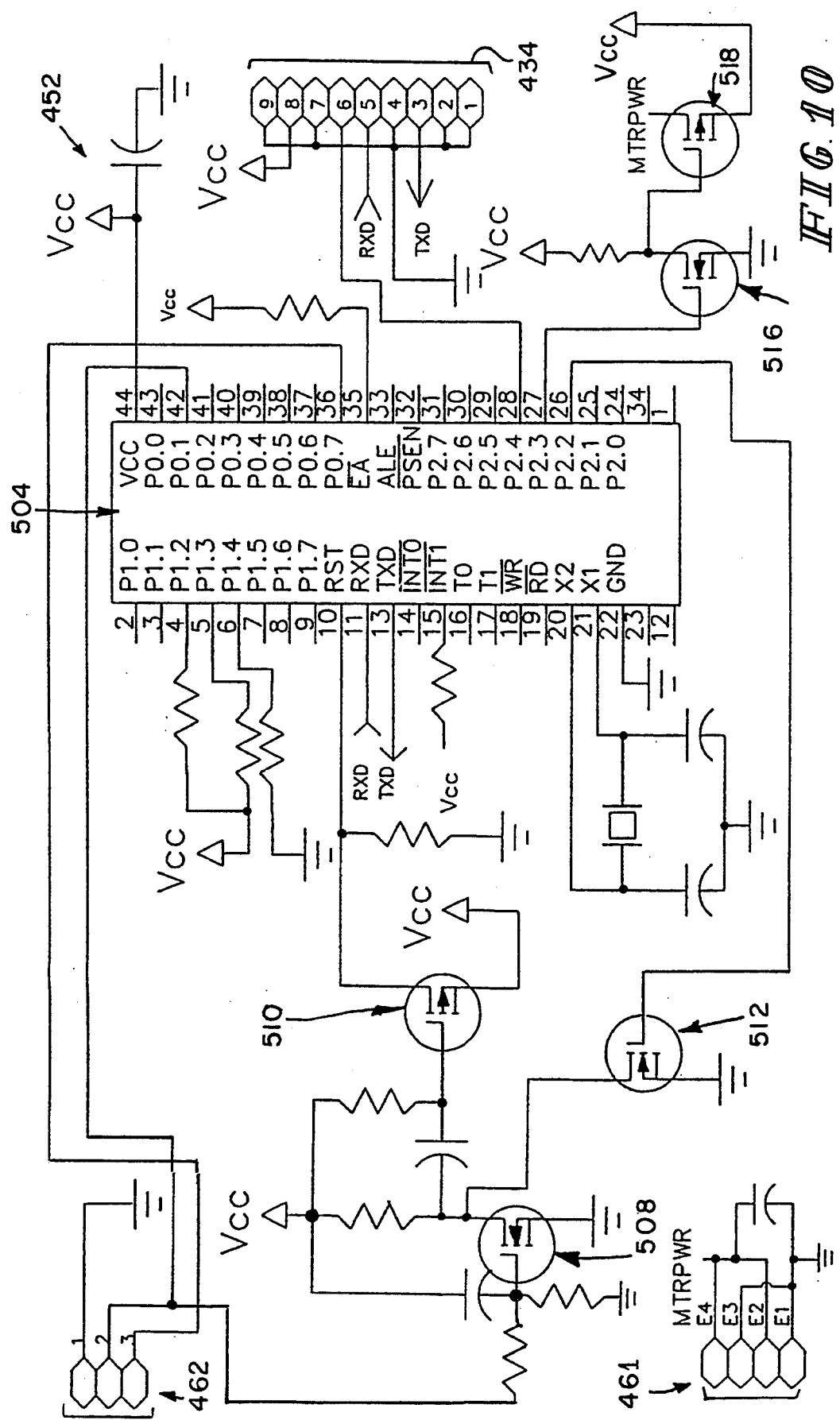
FIG. 10 illustrates in partly block and partly schematic form a circuit contained within the housing of FIG. 9; and, FIG. 11 illustrates in partly block and partly FIG. 9; and, FIG. 1 illustrates in partly block and partly schematic form circuits contained within the instrument of FIG. 1.
Figure 11A:
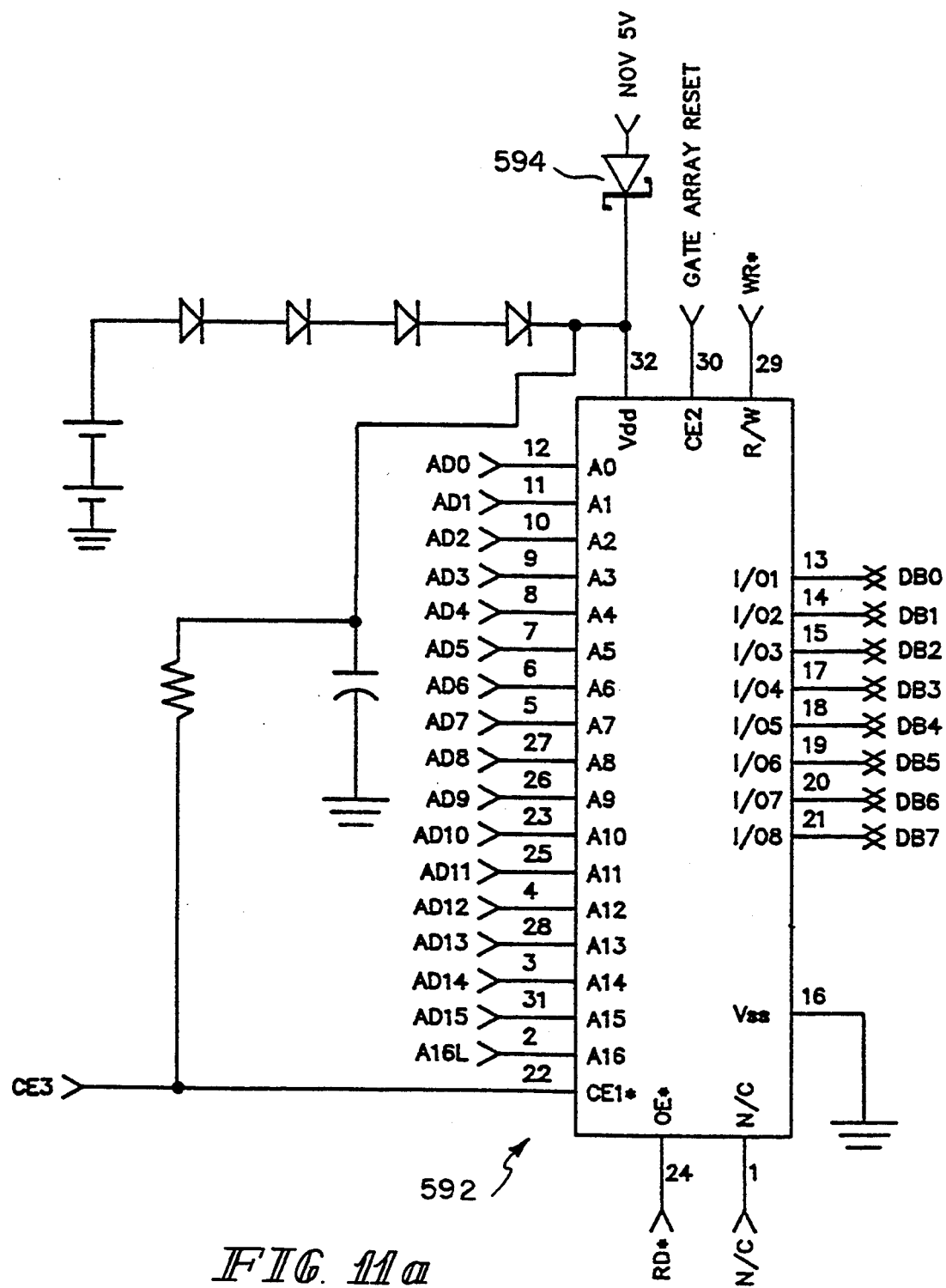
Figure 11B:
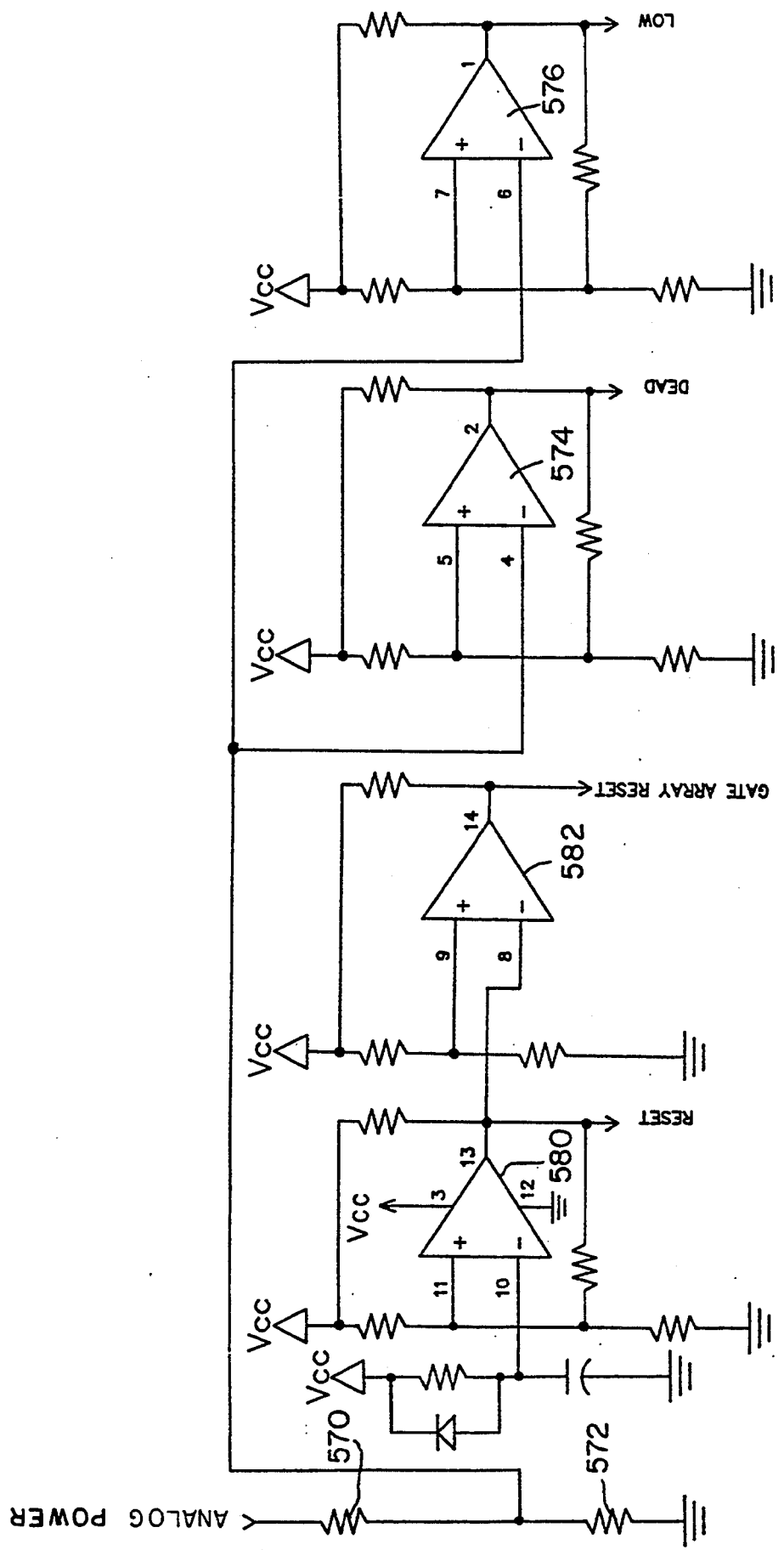
Figure 11C:
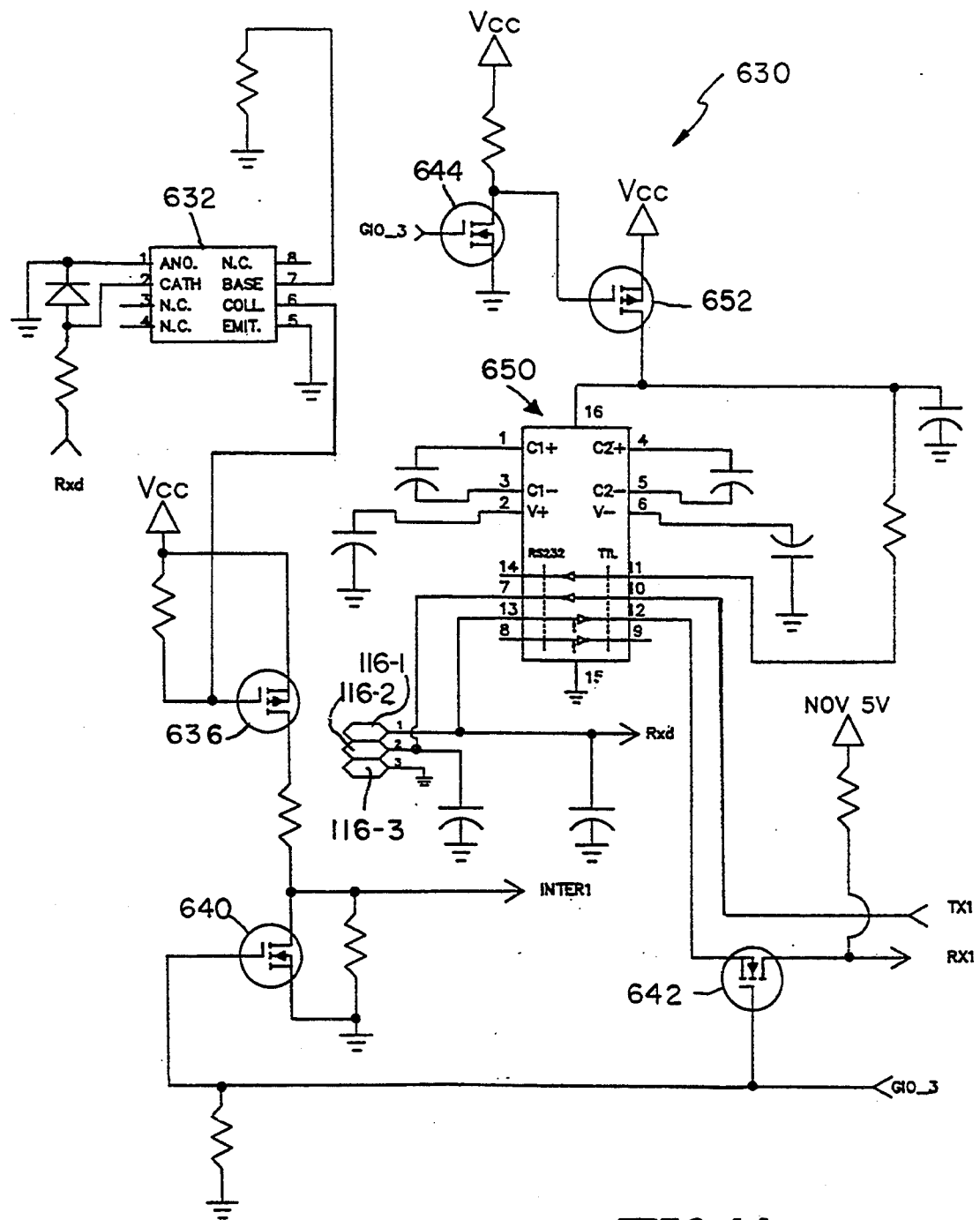
Figure 11D:
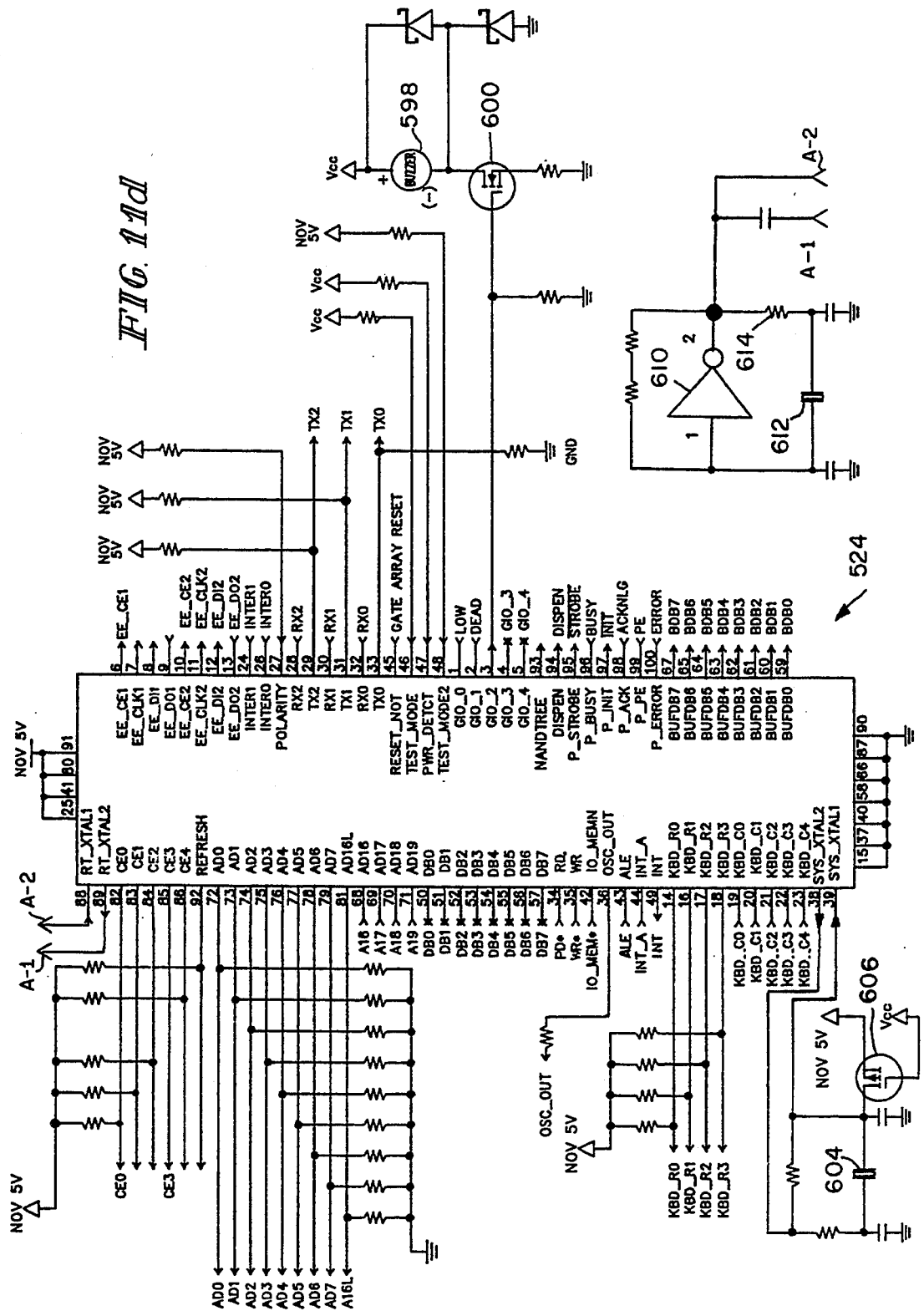
Figure 11E:
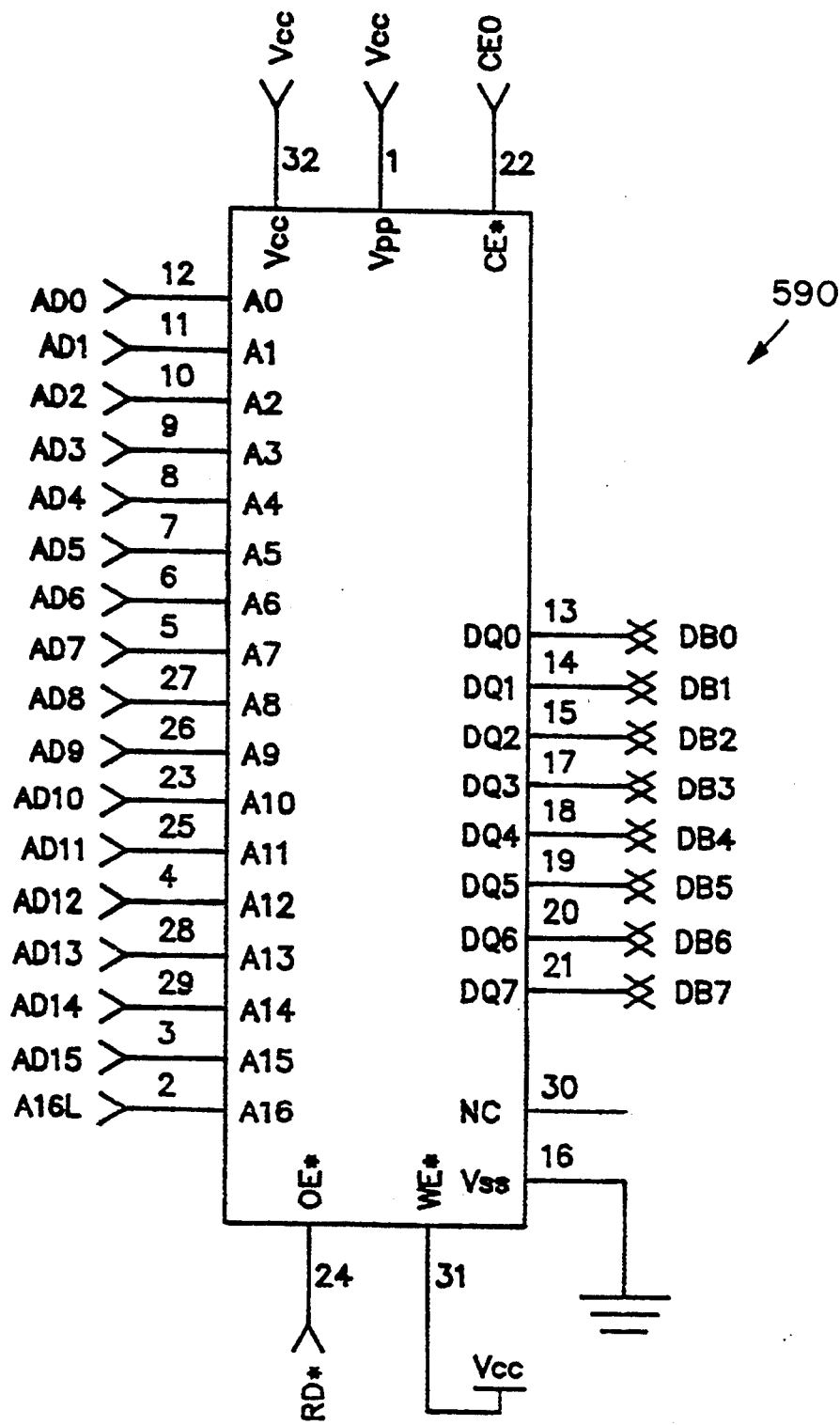
Figure 11F:
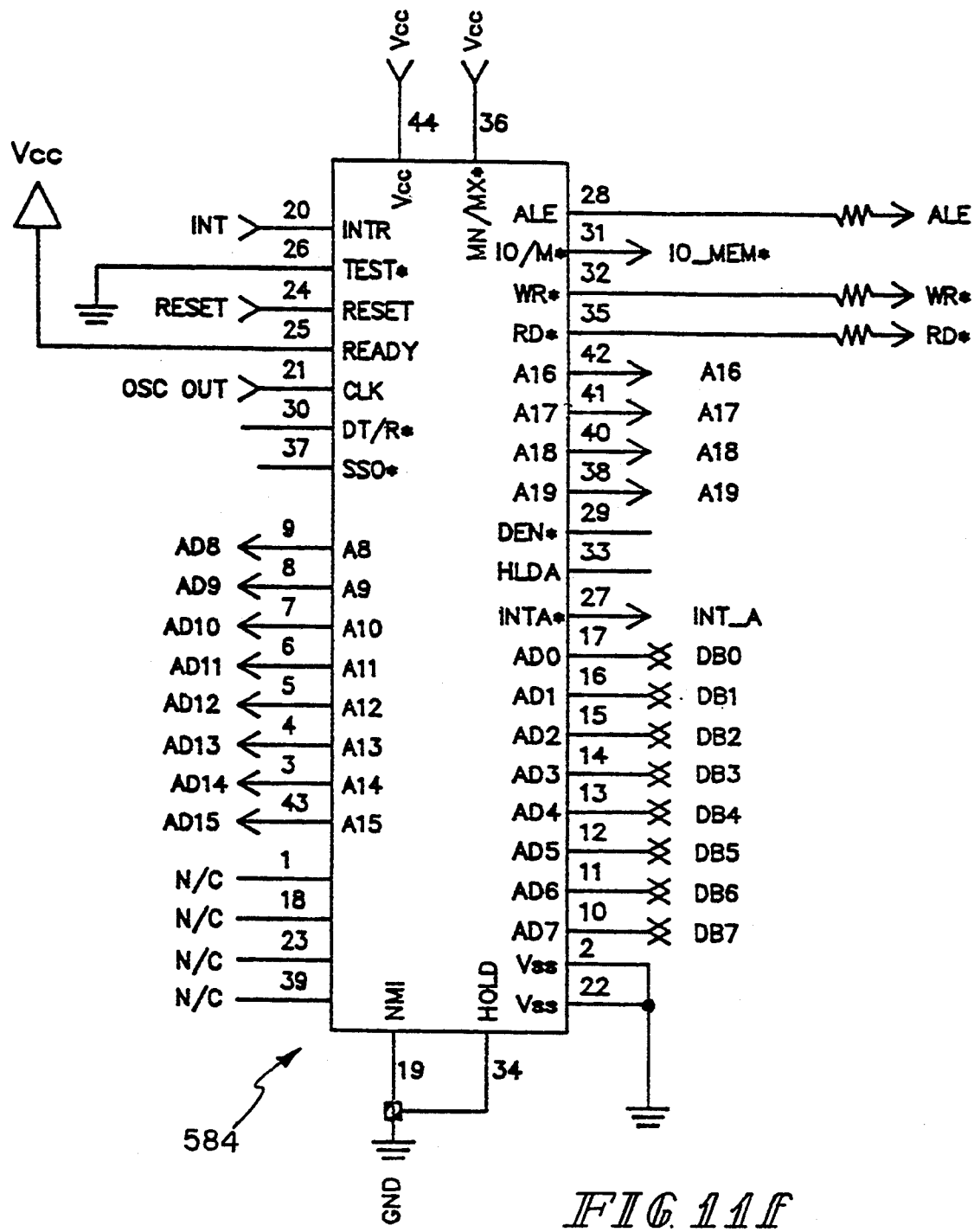
Figure 11G:
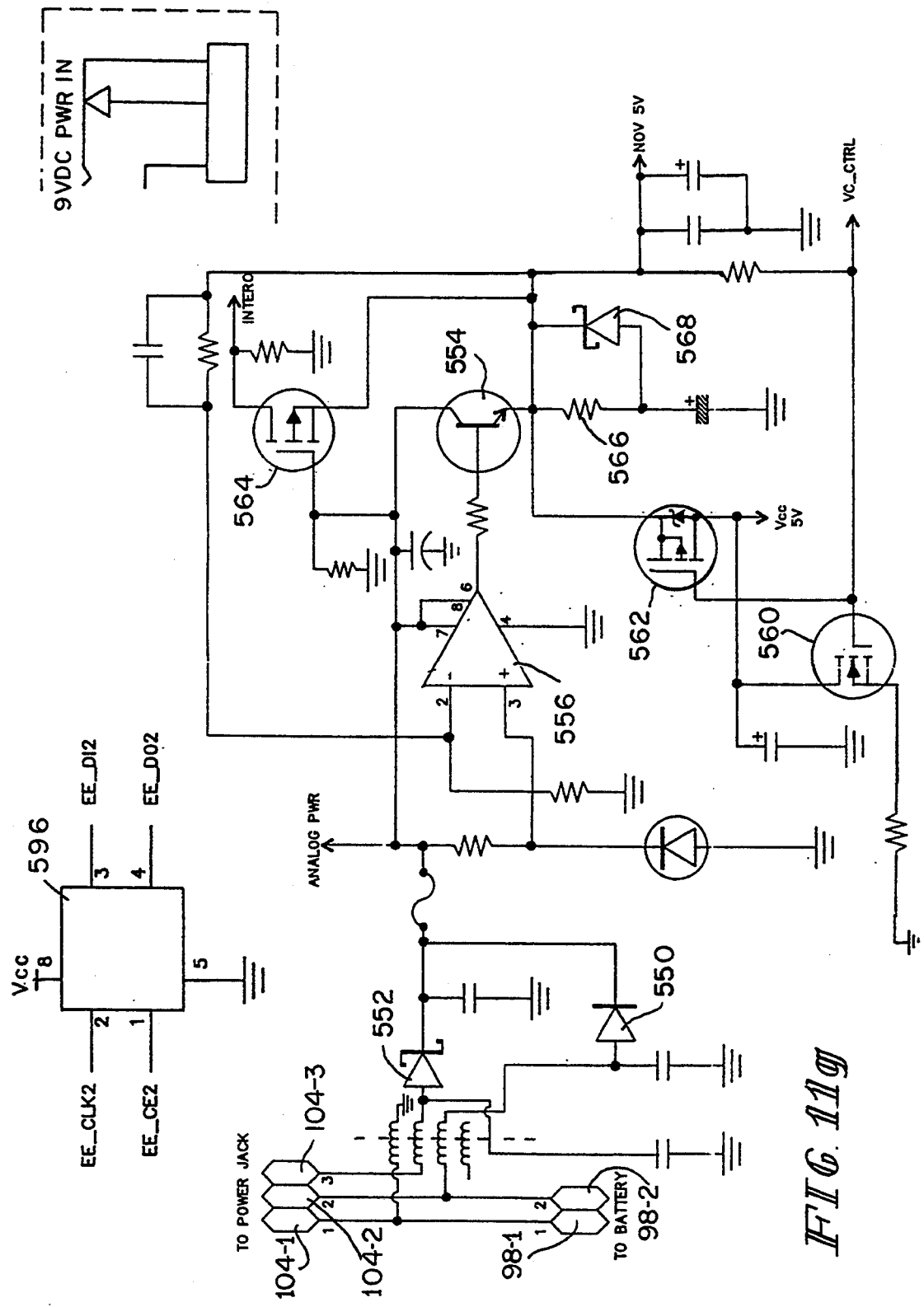
Figure 11I:
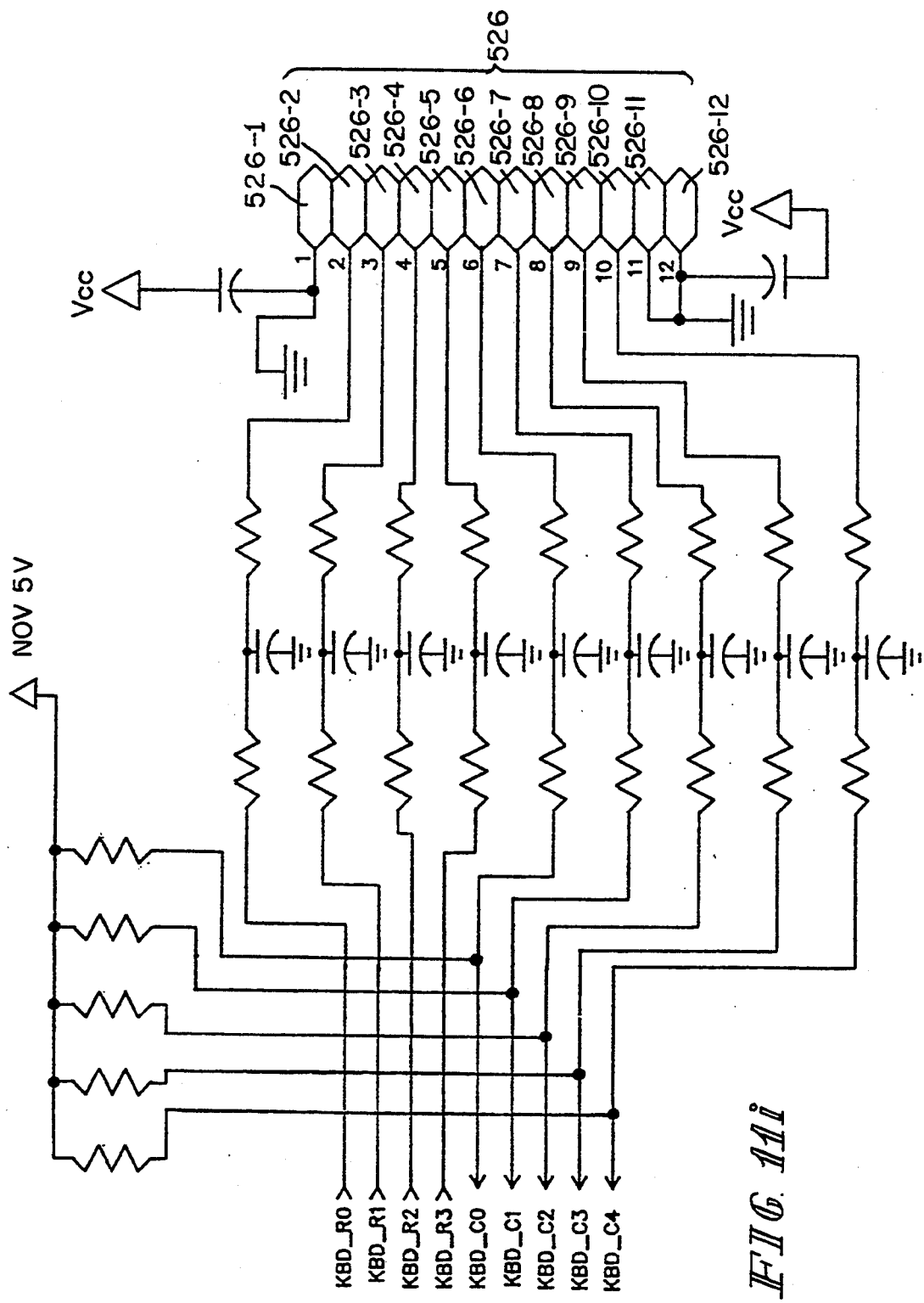
Figure 11J:
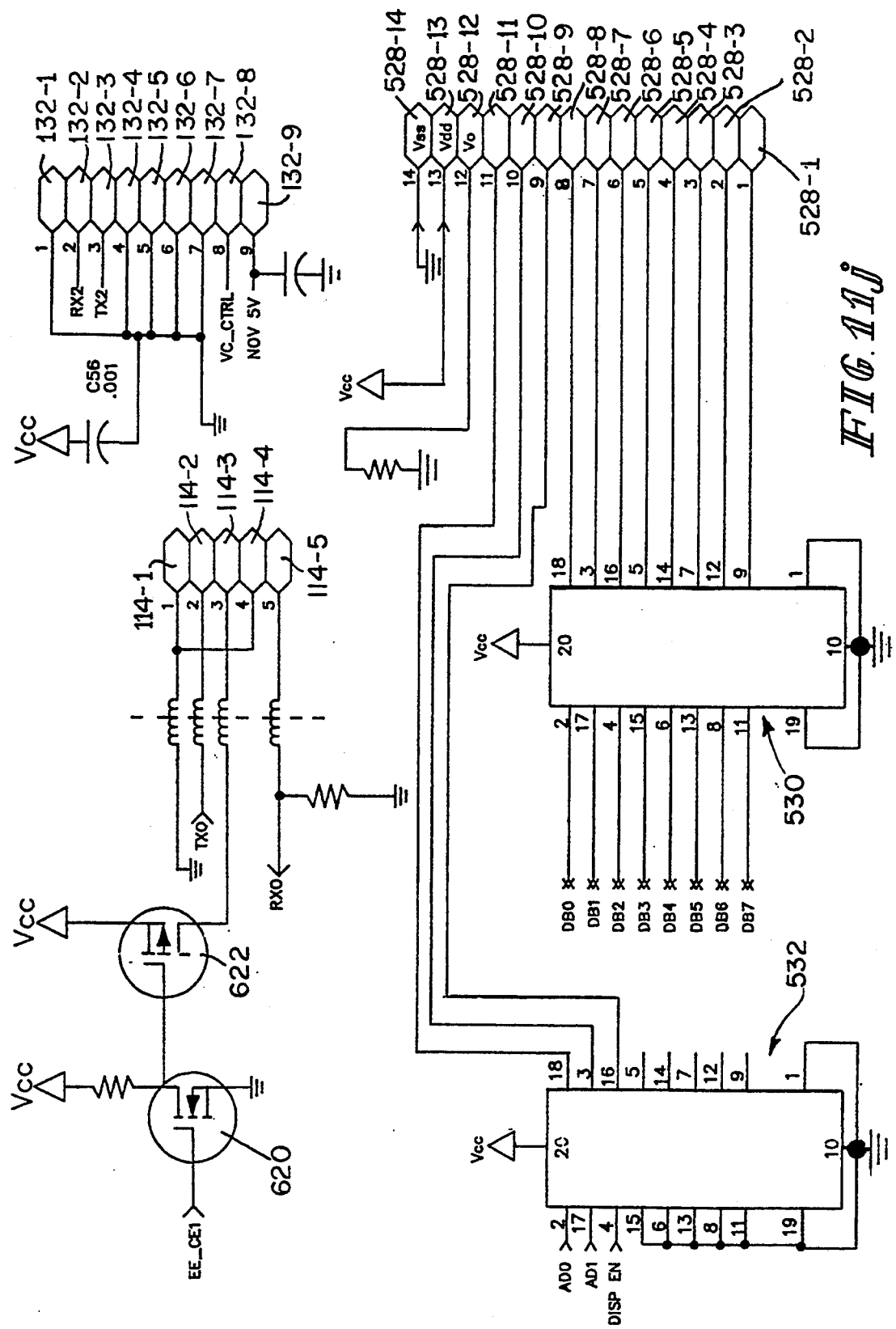

Turning now to FIG. 10, meter 48 is powered by a MeTeRPoWeR potential supply maintained across the two pairs of conductors, pins E2, E4 and E1, E3 associated with battery emulator 461. One pair, E1, E3, of these conductors is also the ACP 452 ground. A 0.001 μF capacitor is coupled between E2, E4 and E1, E3. Meter 48 I/O is provided through the three conductors associated with socket 462. The ACP 452 associated with meter 48 includes an Intel 80C51 μP 504 mounted on PWB 450. The nine pin receptacles on socket 434 are coupled as follows: pin receptacles 1, 2, 4, 7 and 9 to system ground; pin receptacle 3 is the TXD terminal of ACP 452; pin receptacle 5 is the RXD terminal of ACP 452; pin receptacle 6 is coupled to the P2.4 terminal of μP 504; and, pin receptacle 8 is coupled to the $V_{cc}$ supply.

Pin 1 of socket 462 is coupled to the system ground. Pins 2 and 3 of socket 462 are coupled to the P0.1 and P0.7 terminals, respectively, of μP 504. The TXD and RXD terminals, receptacles 3 and 5, respectively, of socket 434 are coupled to the TXD and RXD terminals, respectively, of μP 504. Terminal P0.1 of μP 504 is also coupled through a 100 K resistor to the gate electrode of a type BSS138 FET 508. The gate of FET 508 is coupled to $V_{cc}$ through 0.47 μF capacitor and to ground through a 1M resistor source of FET 508 is grounded. The drain of FET 508 is coupled through a 100 K resistor to $V_{cc}$, through 0.47 μF capacitor to the gate of a type BSS84 FET 510 and directly to the drain of a type BSS138 FET 512. The gate of FET 510 is coupled to $V_{cc}$ through a 100 K resistor. The source of FET 512 is coupled to ground. The gate of FET 512 is coupled to the P2.2 terminal of μP 504. The source of FET 510 is coupled to $V_{cc}$. The drain of FET 510 is coupled to the RST terminal of μP 504 and through a 4.75 K resistor to ground. The INT1 and $\overline{EA}$ terminals of μP 504 are coupled through respective 10 K resistors to $V_{cc}$. The $V_{cc}$ terminal of μP 504 is coupled to $V_{cc}$ and through a 0.1 μF capacitor to ground. The GND terminal of μP 504 is coupled to ground. The P1.2 and P1.3 terminals of μP 504 are coupled through respective 10 K resistors to $V_{cc}$. The P1.4 terminal of μP 504 is coupled through a 100 Ω resistor to ground. The P2.3 terminal of μP 504 is coupled to the gate of a type BSS138 FET 516. The source of FET 516 is coupled to ground, and its drain is coupled through a 1M resistor to $V_{cc}$ and directly to the gate of a type IRFR9020 FET 518. The source of FET 518 is coupled to $V_{cc}$ and the drain of FET 518 is coupled to the MeTeRPoWeR terminal, E2, E4 associated with battery emulator 461.

The primary processor of FIG. 11 is mounted on PCB 64 and communicates through connector 132 with the ACP 150, 250, 350, 450 in a respective housing 124, 126, 128, 130. The primary processor illustratively includes a Toshiba TC 110G11-0262 application-specific integrated circuit (ASIC) 524. The keypad 54 plugs into a socket 526 including contacts 526-1–526-12. Each of contacts 526-2–526-5 is coupled through two respective series 1 K resistors to a respective terminal KBD-R0–KBD-R3 of ASIC 524. Each of terminals KBD-R0–KBD-R3 is coupled through a respective 100 K pull-up resistor to the NOV 5 V supply. The common terminal of each pair of series 1 K resistors is coupled through a respective 68 pF capacitor to ground. Each of contacts 526-6–526-10 is coupled through two respective series 100 resistors to a respective terminal KBD-C0–KBD-C4 of ASIC 524. The common terminal of each pair of series 100 resistors is coupled through a respective 68 pF capacitor to ground. Each of terminals KBD-C0-KBD-C4 is coupled through a respective 15 K pull-up resistor to the NOV 5 V supply. Each of contacts 526-1, 526-11 and 526-12 is coupled to ground and through a 0.001 μF capacitor to $V_{cc}$.

The display 60 plugs into a socket 528 including contacts 528-1–528-14. Each of contacts 528-1–528-8 is coupled to a respective terminal 9, 12 7, 14, 5, 16, 3, 18 of a National Semiconductor 74HC244 buffer integrated circuit 530. Contacts 528-9–528-11 are coupled to respective terminals 16, 3, 18 of a second 74HC244 buffer 532. Terminals 2, 17, 4, 15, 6, 13, 8 and 11 of buffer 530 are coupled to terminals DB0-DB7, respectively, of ASIC 524. Terminals 2, 17 and 4 of buffer 532 are coupled to the AD0, AD1 and DISP EN terminals, respectively, of ASIC 524. Terminals 1, 10 and 19 of both of buffers 530, 532, and terminals 15, 6, 13, 8 and 11 of buffer 532 are all coupled to ground.

The printer port 118 includes contacts 118-1–118-25. Each of contacts 118-2–118-12, 118-15 and 118-16 is coupled through a Fair-Rite Products P.N. 2743019446 or 2743019447 ferrite bead to a terminal BUFDB0-BUFDB7, P-ACK, P-BUSY, P-PE, P-ERROR and P-INIT, respectively, of ASIC 524. Each of terminals 118-1–118-12, 118-15 and 118-16 is coupled to ground through a 0.001 μF capacitor. Terminal 118-1 is coupled through a ferrite bead to the drain terminal of a type BSS138 FET 537 and through a 10 K pull-up resistor to $V_{cc}$. Terminals BUFDB0-BUFDB7, P-ACK, P-BUSY, P-PE, P-ERROR and P-INIT of ASIC 524 are coupled through respective 10 K ⅛W pull-up resistors to the drain of a type BSS84 FET 538. The source of FET 538 is coupled to the NOV 5 V supply The gate of FET 538 is coupled to NOV 5 V through a 100 K resistor and to the drain of a type BSS138 FET 540. The source of FET 540 is coupled to ground. The gate of FET 540 is coupled to the P-INIT terminal of ASIC 524 and through a 100 K resistor to the NOV 5 V supply. Terminals 118-18–118-25 of printer port 118 are coupled to ground and through a 0.001 μF capacitor to $V_{cc}$.

The P-STROBE terminal of ASIC 524 is coupled through a 470 pF capacitor to the gate of a type BSS84 FET 544, and through a 100 K resistor to NOV 5 V. The gate of FET 544 is coupled through a 47.5 K resistor to $V_{cc}$. The source of FET 544 is coupled to $V_{cc}$. The drain of FET 544 is coupled through a 23.7 K resistor to the gate of FET 537. The gate of FET 537 is coupled through a parallel RC circuit including a 23.7 K resistor and a 270 pF capacitor to ground. The source of FET 537 is coupled to ground This circuit-conditions the signal at terminal 118-1 of the printer port 118.

A power supply and regulator circuit includes the battery power socket 98 and external DC supply socket 104. Pins 1 of both of sockets 98, 104 are coupled together. Pins 2 of both of sockets 98, 104 are coupled together. Pins 1 and 2 of sockets 98, 104 and pin 3 of socket 104 are coupled through respective common mode EDS/EMI rejecting inductors wound on a common core. Pins 1 of sockets 98, 104 are coupled through one of these inductors to ground. Pins 2 of sockets 98, 104 are coupled through one of these inductors to the anode of a type SC015-04 diode 550 and through a 0.001 μF capacitor to ground. Pin 3 of socket 104 is coupled through one of these inductors to the anode of a type SE014 Schottky diode 552 and through a 0.001 μF capacitor to ground. The circuit including diodes 550 and 552 is a voltage-steering circuit for the battery and AC adapter. The cathodes of diodes 550, 552 are joined and are coupled through a 0.1 μF capacitor to ground and through a ¾ A fuse to the collector of a Samsung type MJD3055 transistor 554 mounted on a heat sinking metalized area of the primary processor's PCB. The collector of transistor 554 forms the ANALOG PoWeR terminal of the circuit illustrated in FIG. 11. The collector of transistor 554 is coupled through a 200 K resistor to the noninverting (+) input terminal of a Maxim Integrated Products type ICL7611 difference amplifier 556. The output terminal of difference amplifier 556 is coupled through 15 Ω resistor to the base of transistor 554. The emitter of transistor 554 forms the NOV $5^V$ supply terminal of the circuit of FIG. 11 The NOV 5 V terminal is coupled through a parallel RC circuit including a 1M resistor and a 0.1 μF capacitor to the inverting (−) input terminal of difference amplifier 556. The NOV 5 V terminal is also coupled through parallel 0.1 μF and 10 μF tantalum capacitors to ground, and through a 1M resistor to the gates of type BSS138 and type IRFR9020 FETs 560, 562, respectively. The source of FET 560 is coupled through a 10 Ω, ⅛W resistor to ground. The drain of FET 560 is coupled to the $V_{cc}$ supply (+5 VDC) for the GTS 40. The drain of FET 560 is coupled to the drain of FET 562 which forms the $V_{cc}$ supply. The drain of FET 562 is coupled to ground through a 10 μF tantalum capacitor. The source of FET 562 is coupled to the NOV 5 V terminal. The collector of transistor 554 is coupled to the gate of a type BSS84 FET 564 and to ground through a parallel RC circuit including a 0.001 μF capacitor and a 10M resistor. The source of FET 564 is coupled to the NOV 5 V terminal. The drain of FET 564 is coupled to the INTERO terminal of ASIC 524 and to ground through a 1M resistor. FET 564 functions to provide a "power removed" interrupt signal The Nov 5 V terminal is coupled to ground through a series 120 Ω, ¼W resistor 566 and a 0.47 μF capacitor A type SE014 Schottky diode 568 is coupled across resistor 566. The − input terminal of difference amplifier 556 is coupled through a 1M resistor to ground. The + input terminal of difference amplifier 556 is coupled to the cathode of a National Semiconductor type LM385 voltage reference diode, the anode of which is coupled to ground.

The ANALOG PoWeR terminal is coupled through a 332 K resistor 570 and a 200 K resistor 572 in series to ground. The common terminal of resistors 570, 572 is coupled to the − input terminals of two difference amplifiers 574, 576. The output terminals of difference amplifiers 574, 576 are coupled through 4.75 M and 1.5 M resistors, respectively, to their respective +input terminals. The +input and output terminals of difference amplifier 574 are coupled through 137 K and 681 K resistors, respectively, to $V_{cc}$. The +input terminal of difference amplifier 574 is also coupled through a 115 K resistor to ground. The + input and output terminals of difference amplifier 576 are coupled through 124 K and 825 K resistors, respectively, to $V_{cc}$. The + input terminal of difference amplifier 576 is also coupled through a 137 K resistor to ground. The output terminals of difference amplifiers 574 and 576 are coupled to the GIO-1 and GIO-0 terminals, respectively, of ASIC 524.

$V_{cc}$ is coupled through a 200 K resistor to the input terminal of a difference amplifier 580. A 0.33 μF capacitor is coupled between the − input terminal of difference amplifier 580 and ground. A resistive voltage divider including a 100 K resistor and a 105 K resistor is coupled between $V_{cc}$ and ground. The common terminal of these two resistors is coupled to the + input terminal of difference amplifier 580. The output terminal of difference amplifier 580 is coupled through a 4.12M resistor to its + input terminal, through a 576 K resistor to $V_{cc}$ and directly to the − input terminal of a difference amplifier 582. A series resistive voltage divider including two 100 K resistors is coupled between $V_{cc}$ and ground. The common terminal of these resistors is coupled to the + input terminal of difference amplifier 582. The output terminal of difference amplifier 582 is coupled through a 100 K resistor to $V_{cc}$. The output terminals of difference amplifiers 580, 582 are coupled to the RESET terminal of an OKI 80C88 microprocessor (μP) 584 and to the RESET-NOT terminal of ASIC 524, respectively. Difference amplifiers 574, 576, 580 and 582 illustratively are type LP339M difference amplifiers The READY, $V_{cc}$ and MN/MX* terminals of μP 584 are coupled to $V_{cc}$. The TEST, NMI, HOLD and $V_{ss}$ terminals of μP 584 are coupled to ground. The ALE, WR*, CLK and RD, terminals of μP 584 are coupled through respective 51.1 Ω resistors to the ALE, WR, OSC OUT and RD terminals, respectively, of ASIC 524. The IO/M* terminal of μP 584 is coupled to the IO-MEMN terminal of ASI 524. The A16–A19 terminals of μP 584 are coupled to the A16–A19 terminals, respectively, of ASIC 524. The INTA* terminal of μP 584 is coupled to the INT-A terminal of ASIC 524. The AD0–AD7 terminals of μP 584 are coupled to the DB0–DB7 terminals, respectively, of ASIC 524. The A8–A15 terminals of μP 584 are coupled to the A8–A15 terminals, respectively, of a Signetics type 27C010 programmable read-only memory (PROM) 590. The INTR terminal of μP 584 is coupled to the INT terminal of ASIC 524.

The AD0–AD7 and AD16L terminals of ASIC 524 are coupled through respective 100 K pull-down resistors to ground. Terminals AD0–AD7 and AD16L of ASIC 524 are also coupled to terminals A0–A7 and A16, respectively, of PROM 590. Terminals DQ0–DQ7 of PROM 590 are coupled to terminals DB0–DB7 of ASIC 524. Terminal CE* of PROM 590 is coupled to the CE0 terminal of ASIC 524. Terminal OE* of PROM 590 is coupled to the RD terminal of ASIC 524. Terminals WE*, $V_{cc}$ and $V_{pp}$ of PROM 590 are coupled to $V_{cc}$. Terminal $V_{ss}$ of PROM 590 is coupled to ground.

A Hitachi type HM628128LFP-12 static random access memory (RAM) 592 includes I/O1–I/O8 terminals coupled to terminals DB0–DB7, respectively, of ASIC 524. Terminals A0–A16 of RAM 592 are coupled to terminals A0–A16, respectively, of PROM 590. NOV 5 V supply is coupled through a type SE014 Schottky diode 594 to the $V_{dd}$ terminal of RAM 592. Terminal $V_{dd}$ is also coupled through 0.47 μF capacitor to ground, and through a 100 K resistor to terminal CE1, of RAM 592. Terminal CE1* of RAM 592 is coupled to terminal CE3 of ASIC 524. Power for RAM 592 when NOV 5 V is not available is supplied from two series type CR4250-FT5-4 dry cells through four series type MMBD914L diodes to the $V_{dd}$ terminal of RAM 592. Terminal CE2 of RAM 592 is coupled to GATE ARRAY RESET, the output terminal of difference amplifier 582. The R/W terminal of RAM 592 is coupled to the WR terminal of ASIC 524. The $V_{ss}$ terminal of RAM 592 is grounded.

The CE0–CE2, CE4 and REFRESH terminals of ASIC 524 are coupled through respective 100 K resistors to NOV 5 V. The EE-CE2, EE-CLK2, EE-DI2 and EE-DO2 terminals of ASIC 524 are coupled to pins 1, 2, 3 and 4, respectively, of a Samsung type KM93C46GD electronically erasable, programmable read-only memory (EEPROM) 596. The POLARITY, TX2 and TX1 terminals of ASIC 524 are coupled through respective 100 K resistors to NOV 5 V. The TX0 terminal of ASIC 524 is coupled through a 100 K resistor to ground. The TEST MODE, PWR DETCT and TEST MODE 2 terminals of ASIC 524 are coupled through respective 100 K resistors to $V_{cc}$, $V_{cc}$ and NOV 5 V, respectively. The GIO-2 terminal of ASIC 524 is coupled to the gate of a buzzer 598-driver type BSS138 FET 600. The drain of FET 600 is coupled to the − terminal of a Mallory type MCP320B2 buzzer 598, the + terminal of which is coupled to $V_{cc}$. The source of FET 600 is coupled through a 124 Ω, ⅛W resistor to ground. Type SE014 Schottky diodes are coupled across buzzer 598 and the drain of FET 600 to ground. The gate of FET 100 is coupled to ground through a 100 K resistor.

The necessary time bases for the circuit illustrated in FIG. 11 are generated by crystal oscillator circuits associated with the ASIC 524. In a first of these, a 1 K resistor and 3.6864 MHz crystal 604 are coupled in series across the SYS-XTAL1 and SYS-XTAL2 terminals of ASIC 524. NOV 5 V is coupled to the source of a type BSS84 4FET 606, the drain of which is coupled to the SYS-XTAL1 terminal. The gate of FET 604 is coupled to $V_{cc}$. Both terminals of crystal 604 are coupled to ground through 33 pF capacitors. A 1M resistor is coupled across the SYS-XTAL1 and SYS-XTAL2 terminals.

In the second of the time base generators, a 470 pF capacitor is coupled across the RT-XTAL1 and RT-XTAL2 terminals of ASIC 524. This time base generator is the day/date timer. The output terminal of an inverter 610, such as one inverter of a type 74HC04 hex inverter, is coupled to the RT-XTAL1 terminal. A 32.768 KHz crystal 612 and 475 K resistor 614 in series are coupled between the input and output terminals of inverter 610. A 2M resistor is also coupled between the input and output terminals of inverter 610. A 22 pF capacitor is coupled between the inverter 610 input terminal and ground. A 33 pF capacitor is coupled between the common terminal of crystal 612 and resistor 614 and ground.

The EE-CE1 terminal of ASIC 524 is coupled to the gate of a type BSS138 FET 620. The source of FET 620 is coupled to ground. The drain of FET 620 is coupled directly to the gate of a type BSS84 FET 622 and through a 475 K resistor to $V_{cc}$. The source of FET 622 is coupled to V. The drain of FET 622 is coupled through an ESD/EMI common mode rejection inductor device to a terminal, pin 114-3, of the bar code reader socket 114. Another inductor of the common mode rejection device is coupled to ground at one end and to pins 114-1 and 114-4 of the bar code reader socket 114 at its other end. Pins 114-2 and 114-5 of the bar code reader socket 114 are coupled through respective inductors of the common mode rejection device to the TX0 and RX0 terminals, respectively, of ASIC 524. The RX0 terminal is also coupled through a 1 K resistor to ground.

Socket 132 includes pins 132-1, -4, -5, -6 and -7 coupled to ground and through a 0.001 μF capacitor to $V_{cc}$.

Pins 132-2 and 132-3 of socket 132 are coupled to terminals RX2 and TX2, respectively, of ASIC 524. Pin 132-8 of socket 132 is coupled to the gate of FET 560. Pin 132-9 of socket 132 is coupled to NOV 5 V and through a 0.001 µF capacitor to ground.

Communication line drivers dissipate considerable power. In a normally battery powered system, such as GTS 40, such dissipation must be kept to a minimum to enhance battery life. In GTS 40, a circuit 630 monitors the RS232 communication channel through port 108 and only switches the line drivers on when communication is established. When no signal is present on RS232 port 108, the circuit 630 consumes no power. Once a signal is detected at the RS232 port 108, circuit 630 turns itself on and signals the ASIC 524. The ASIC 524 acknowledges by toggling one of the contacts of the RS232 port 108. Circuit 630 consumes power until the system is reset.

Circuit 630 includes a Motorola type MOC. optical coupler 632, pin 2 of which is coupled through a 698 resistor to contact 116-1 of RS232 port 108. Pin 2 of optical coupler 632 is coupled to the anode of a diode 634, the cathode of which is coupled to pin 1 of optical coupler 632 and to ground. Pin 5 of optical coupler 632 is coupled directly to ground. Pin 7 of optical coupler 632 is coupled through a 1M resistor to ground. Pin 6 of optical coupler 632 is coupled to the gate of a type BSS84 FET 636 and through a 47.5 K resistor to $V_{cc}$. The source of FET 636 is coupled to $V_{cc}$. The drain of FET 636 is coupled through a 47.5 K resistor to the INTER1 terminal of ASIC 524, and to ground through a 475 K resistor. The GIO-3 terminal of ASIC 524 is coupled to the gates of three type BSS138 FETs 640, 642, 644 and to ground through a 100 K resistor. The source of FET 640 is coupled to ground, and its drain is coupled to the INTER1 terminal of ASIC 524. The drain of FET 642 is coupled to the RX1 terminal of ASIC 524, and through a 100 K pull-up resistor to NOV 5 V. The source of FET 642 is coupled to an output terminal, pin 12, of a Linear Technology type LT1281 RS232-to-TTL/TTL-to-RS232 interface integrated circuit 650. The TX1 terminal of ASIC 524 is coupled to pin 10 of interface 650. Pin 7 of interface 650 is coupled to a contact 116-2 of RS232 port 108. Pin 13 of interface 650 is coupled to contact 116-1 of port 108. Contact 116-3 of port 108 is coupled to ground. 0.001 µF capacitors are coupled between each of pins 116-1 and 116-2 and ground. 1 µF capacitors are coupled between each of terminals V+ and V− of interface 650 and ground. Respective 0.1 µF capacitors are coupled across the C1+ and C1− terminals and across the C2+ and C2− terminals of interface 650. The drain of FET 644 is coupled directly to the gate of a type BSS84 FET 652 and through a 475 K resistor to $V_{cc}$. The source of FET 652 is coupled to $V_{cc}$. The drain of FET 652 is coupled to pin 16 of interface 650 through a 0.1 µF capacitor to ground and through a 47.5 K resistor pin 11 of interface 650.

In operation, circuit 630 will remain off and not consume any power as long as no signal appears on pin 116-1 of port 108. The remaining circuitry of GTS 40 can function normally with circuit 630 off. When a negative Rxd signal arrives on pin 116-1 of port 108, however FET 636 is turned on by the output from optical coupler 632. The INTER1 signal generated by turning on FET 636 is acknowledged by the ASIC 524 raising its terminal GIO-3. This turns FET 640 on, masking further interrupts on INTER1. It also turns FETs 644 and 652 on, supplying $V_{cc}$ to pin 16 of interface 650. Finally, it turns FET 642 on, permitting current to flow from its drain to its source when pin 12 of interface 650 sinks current (when signal is present). This permits the drain voltage of FET 642 to drop from NOV 5 V.

What is claimed is:

1. A system for adapting one of a number of different types of instruments to a common protocol, each instrument having a first serial input-output (I/O) port, first means for controlling the serial I/O port, and second means for furnishing operating power to the instrument, the system including a different type of housing for each different type of instrument, each different type of housing including means defining openings through which selected controls and displays of a respective one of the instruments are accessible, each different type of housing including third means for coupling to a respective type of instrument's first serial I/O port, fourth means for coupling to a respective type of instrument's second means, and a data processing module including a first multiple conductor connector, each type of housing including a complementary second multiple conductor connector for connecting to the first multiple conductor connector when a respective housing is mated to the data processing module.

2. The system of claim 1 wherein the second means comprises a battery enclosure having first and second battery terminals, and the fourth means comprises a battery emulator having third and fourth terminals for engagement by the first and second battery terminals, respectively, when an instrument of the respective type is housed in a housing of the respective type, and fifth means for coupling the third and fourth terminals across a source of operating power for the respective instrument.

3. A system for adapting one of a number of different types of instruments to a common protocol, each instrument having a first serial input-output (I/O) port, first means for controlling the serial I/O port, and second means for furnishing operating power to the instrument, the system including a different type of housing for each different type of instrument, each different type of housing including means defining openings through which selected controls and displays of a respective one of the instruments are accessible, each different type of housing including third means for coupling to a respective type of instrument's first serial I/O port and fourth means for coupling to a respective type of instrument's second means, the openings including an opening for an on/off control for a respective instrument, an opening for a prompt/test results display for the respective instrument, and an opening for insertion of unreacted/reacted test strips for the respective instrument.

4. The system of claim 3 wherein the openings further include an opening through which access to a timer control for a respective instrument can be achieved.

5. A system for adapting one of a number of different types of instruments to a common protocol, each instrument having a first serial input-output (I/O) port, first means for controlling the serial I/O port, and second means for furnishing operating power to the instrument, the system including a different type of housing for each different type of instrument, each different type of housing including means defining openings through which selected controls and displays of a respective one of the instruments are accessible, each different type of housing including third means for coupling to a respective type of instrument's first serial I/O port and fourth means for coupling to a respective type of instrument's second means, the third means comprising a first microprocessor, sixth means for conditioning the signals at the first I/O port, seventh means for coupling the first I/O port to the sixth means, and eighth means for coupling the sixth means to the first microprocessor.

6. The system of claim 1 or 5 wherein the data processsing module further comprises first slide members, and each type of housing further comprises complementary second slide members for engagement with the first slide members when a respective housing engages the data processing module.

7. The system of claim 1 or 5 wherein the data processing module further comprises a data processing module power supply and ninth means for coupling the power supply across a pair of conductors of the first multiple conductor connector, mating of a respective housing to the data processing module connecting that respective housing, its respective first microprocessor, and a respective instrument housed in that respective housing to the data processing module power supply.

8. The system of claim 1 or 5 wherein the data processing module further comprises tenth means for coupling the data processing module to an external power supply, and eleventh means for coupling the external power supply across a pair of conductors of the first multiple conductor connector, mating of a respective housing to the data processing module connecting that respective housing, its respective first microprocessor, and a respective instrument housed in that respective housing to the external power supply.

9. The system of claim 1 or 5 wherein the data processing module further comprises a second microprocessor having a second microprocessor I/O, a second serial I/O port, twelfth means for coupling respective conductors of the first multiple conductor connector across a first group of pins of the second microprocessor I/O, and thirteenth means for coupling a second group of pins of the second microprocessor I/O to respective terminals of the second serial I/O port.

10. The system of claim 9 wherein the thirteenth means comprises an RS232-to-transistor-transistor logic (TTL)/TTL-to-RS232 interface.

11. The system of claim 10 wherein the thirteenth means comprises an optical isolator, a receive data terminal of the second serial I/O port coupled to a light source portion of the optical isolator, and fourteenth means for coupling a light activated switch portion of the optical isolator to an RS232-to-TTL received data output terminal of the RS232-to-TTL/TTL-to-RS232 interface.

12. The system of claim 11 wherein the fourteenth means comprises an interrupt pin of the second microprocessor I/O.

13. The system of claim 11 and further comprising fifteenth means for switching power to he RS232-to-TTL/TTL-to RS232 interface, the fifteenth means coupled to the second means, to an operating power supply terminal of the RS232-to-TTL/TTL-to-RS232 interface, and to the interrupt pin of the second microprocessor I/O, receipt of data on the receive data terminal of the second serial I/O port causing power to be supplied from the second means to the operating power supply terminal of the RS232-to-TTL/TTL-to-RS232 interface to activate the RS232-to-TTL/TTL-to-RS232 interface and to activate a switch in the RS232-to-TTL output terminal of the RS232-to-TTL/TTL-to-RS232 interface.

14. A system for adapting one of a number of different types of instruments to a common protocol, each instrument having a first serial input-output (I/O) port, first means for controlling the serial I/O port, and second means for furnishing operating power to the instrument, the system including a different type of housing for each different type of instrument, each different type of housing including means defining openings through which selected controls and displays of a respective one of the instruments are accessible, each different type of housing including third means for coupling to a respective type of instrument's first serial I/O port and fourth means for coupling to a respective type of instrument's second means, the openings including an opening for a prompt/test results display for the respective instrument, and an opening for insertion of unreacted/reacted test strips for the respective instrument.

15. The system of claim 14 wherein the openings further include an opening through which access to a timer control for a respective instrument can be achieved.

16. The system of claim 14 or 15 wherein the openings further include an opening through which an on/off control for a respective instrument can be accessed.

17. A system for adapting one of a number of different types of instruments to a common protocol, each different type of instrument being for determining the concentration of a medically significant component of a body fluid, each instrument having a first serial input-output (I/O) port, first means for controlling the serial I/O port, and second means for furnishing operating power to the instrument, the system including a different type of housing for each different type of instrument, each different type of housing including means defining openings through which selected controls and displays of a respective one of the instruments are accessible, each different type of housing including third means for coupling to a respective type of instrument's first serial I/O port and fourth means for coupling to a respective type of instrument's second means, a data processing module including a first multiple conductor connector, each type of housing including a complementary second multiple conductor connector for connecting to the first multiple conductor connector when a respective housing is mated to the data processing module.

18. The system of claim 17 wherein each different type of instrument determines the concentration of the medically significant component by determining a characteristic of a chemical reaction of the medically significant component with a reagent supported on a test strip, each different type of housing further including means defining an opening through which unreacted/reacted test strips can be inserted into a respective different type of instrument.

19. The system of claim 17 or 18 wherein each different type of housing further includes an opening through which a display of a respective different type of instrument can be viewed.

20. The system of claim 17 or 18 wherein the second means comprises a battery enclosure having first and second battery terminals, and the fourth means comprises a battery emulator having third and fourth terminals for engagement by the first and second battery terminals, respectively, when an instrument of the respective type is housed in a housing of the respective type, and fifth means for coupling the third and fourth terminals across a source of operating power for the respective instrument.

21. A system for adapting one of a number of different types of instruments to a common protocol, each different type of instrument being for determining the concentration of a medically significant component of a body fluid, each instrument having a first serial input-output (I/O) port, first means for controlling the serial I/O port, and second means for furnishing operating power to the instrument, the system including a different type of housing for each different type of instrument, each different type of housing including means defining openings through which selected controls and displays of a respective one of the instruments are accessible, each different type of housing including third means for coupling to a respective type of instrument's first serial I/O port and fourth means for coupling to a respective type of instrument's second means, the third means comprising a first microprocessor, sixth means for conditioning the sinals at the first I/O port, seventh means for coupling the first I/O port to the sixth means, and eighth means for coupling the sixth means to the first microprocessor.

22. The system of claim 17 and 21 wherein the data processing module further comprises first slide members, and each type of housing further comprises complementary second slide members for engagement with the first slide members when a respective housing engages the data processing module.

23. The system of claim 17 or 21 wherein the data processing module further comprises a data processing module power supply and ninth means for coupling the power supply across a pair of conductors of the first multiple conductor connector, mating of a respective housing to the data processing module connecting that respective housing, its respective first microprocessor, and a respective instrument housed in that respective housing to the data processing module power supply.

24. The system of claim 17 or 21 wherein the data processing module further comprises tenth means for coupling the data processing module to an external power supply, and eleventh means for coupling the external power supply across a pair of conductors of the first multiple conductor connector, mating of a respective housing to the data processing module connecting that respective housing, its respective first microprocessor, and a respective instrument housed in that respective housing to the external power supply.

25. The system of claim 17 or 21 wherein the data processing module further comprises a second microprocessor having a second microprocessor I/O, a second serial I/O port, twelfth means for coupling respective conductors of the first multiple conductor connector across a first group of pins of the second microprocessor I/O, and thirteenth means for coupling a second group of pins of the second microprocessor I/O to respective terminals of the second serial I/O port.

26. The system of claim 25 wherein the thirteenth means comprises an RS232-to-transistor-transistor logic (TTL)/TTL-to-RS232 interface.

27. The system of claim 26 wherein the thirteenth means comprises an optical isolator, a receive data terminal of the second serial I/O port coupled to a light source portion of the optical isolator, and fourteenth means for coupling a light activated switch portion of the optical isolator to an RS232-to-TTL received data output terminal of the RS232-to-TTL/TTL-to-RS232 interface.

28. The system of claim 27 wherein the fourteenth means comprises an interrupt pin of the second microprocessor I/O.

29. The system of claim 27 and further comprising fifteenth means for switching power to the RS232-to-TTL/TTL-to-RS232 interface, the fifteenth means coupled to the second means, to an operating power supply terminal of the RS232-to-TTL/TTL-to-RS232 interface, and to the interrupt pin of the second microprocessor I/O, receipt of data on the receive data terminal of the second serial I/O port causing power to be supplied from the second means to the operating power supply terminal of the RS232-to-TTL/TTL-to-RS232 interface to activate the RS232-to-TTL/TTL-to-RS232 interface and to activate a switch in the RS232-to-TTL output terminal of the RS232-to-TTL/TTL-to-RS232 interface.

* * * * *